(12) United States Patent
Bergheim et al.

(10) Patent No.: US 8,790,396 B2
(45) Date of Patent: Jul. 29, 2014

(54) METHODS AND SYSTEMS FOR CARDIAC VALVE DELIVERY

(75) Inventors: Bjarne Bergheim, Laguna Hills, CA (US); Walter Cuevas, Lake Forest, CA (US); Jeffrey P. DuMontelle, Irvine, CA (US)

(73) Assignee: Medtronic 3F Therapeutics, Inc., Irvine, CA (US)

( * ) Notice: Subject to any disclaimer, the term of this patent is extended or adjusted under 35 U.S.C. 154(b) by 882 days.

(21) Appl. No.: 11/492,486

(22) Filed: Jul. 24, 2006

(65) Prior Publication Data
US 2007/0027534 A1    Feb. 1, 2007

Related U.S. Application Data

(60) Provisional application No. 60/702,892, filed on Jul. 27, 2005, provisional application No. 60/717,879, filed on Sep. 16, 2005, provisional application No. 60/734,429, filed on Nov. 8, 2005, provisional application No. 60/740,694, filed on Nov. 29, 2005, provisional application No. 60/762,909, filed on Jan. 27, 2006.

(51) Int. Cl.
*A61F 2/24*    (2006.01)

(52) U.S. Cl.
USPC ........................................ 623/2.11

(58) Field of Classification Search
USPC ............... 623/1.11, 1.12, 2.11; 606/108, 200, 606/191–199; 604/104, 509, 96.01, 528, 604/141, 142, 912, 915–919, 103.07, 95.03, 604/101.01–101.05, 103; 600/138, 144
See application file for complete search history.

(56) References Cited

U.S. PATENT DOCUMENTS

| | | | | |
|---|---|---|---|---|
| 4,423,725 A | * | 1/1984 | Baran et al. | 128/207.15 |
| 4,432,349 A | * | 2/1984 | Oshiro | 600/141 |
| 4,771,777 A | * | 9/1988 | Horzewski et al. | 606/194 |
| 4,795,427 A | * | 1/1989 | Helzel | 604/9 |
| 5,158,086 A | * | 10/1992 | Brown et al. | 600/459 |
| 5,252,159 A | * | 10/1993 | Arney | 156/169 |
| 5,386,816 A | * | 2/1995 | Inoue et al. | 600/121 |
| 5,421,826 A | * | 6/1995 | Crocker et al. | 604/509 |
| 5,448,989 A | * | 9/1995 | Heckele | 600/142 |
| 5,554,119 A | * | 9/1996 | Harrison et al. | 604/103.01 |

(Continued)

FOREIGN PATENT DOCUMENTS

| | | |
|---|---|---|
| WO | WO2004/089253 | 10/2004 |
| WO | WO2004/103223 | 12/2004 |
| WO | WO2006/005015 | 1/2006 |

OTHER PUBLICATIONS

Supplemental European Search Report, European Patent Office, Mar. 5, 2013.

*Primary Examiner* — Corrine M McDermott
*Assistant Examiner* — Christopher L Templeton

(57) ABSTRACT

The present invention provides systems and methods for the repair, removal, and/or replacement of heart valves. The methods comprise introducing a delivery system into the heart, wherein a prosthesis is disposed on the delivery member attached to the delivery system, advancing the prosthesis to the target site, and disengaging the prosthesis from the delivery member at the target site for implantation. The present invention also provides implant systems for delivering a prosthesis to a target site in or near the heart. In one embodiment of the present invention, the implant system comprises a delivery system, an access system, and a prosthesis.

26 Claims, 16 Drawing Sheets

(56) References Cited

U.S. PATENT DOCUMENTS

| | | | | |
|---|---|---|---|---|
| 5,558,642 | A * | 9/1996 | Schweich et al. | 604/103.01 |
| 5,613,948 | A * | 3/1997 | Avellanet | 604/103.07 |
| 5,843,027 | A * | 12/1998 | Stone et al. | 604/509 |
| 5,972,030 | A * | 10/1999 | Garrison et al. | 623/2.11 |
| 5,984,959 | A | 11/1999 | Robertson et al. | |
| 6,007,517 | A * | 12/1999 | Anderson | 604/103.04 |
| 6,015,402 | A * | 1/2000 | Sahota | 604/523 |
| 6,027,510 | A * | 2/2000 | Alt | 606/108 |
| 6,056,722 | A * | 5/2000 | Jayaraman | 604/102.01 |
| 6,126,649 | A * | 10/2000 | VanTassel et al. | 604/528 |
| 6,139,517 | A * | 10/2000 | Macoviak et al. | 604/8 |
| 6,143,015 | A * | 11/2000 | Nobles | 606/194 |
| 6,190,406 | B1 * | 2/2001 | Duerig et al. | 623/1.2 |
| 6,364,900 | B1 * | 4/2002 | Heuser | 623/1.11 |
| 6,425,916 | B1 | 7/2002 | Garrison et al. | |
| 6,730,118 | B2 * | 5/2004 | Spenser et al. | 623/1.24 |
| 6,736,841 | B2 * | 5/2004 | Musbach et al. | 623/1.11 |
| 6,780,199 | B2 * | 8/2004 | Solar et al. | 623/1.11 |
| 6,908,481 | B2 * | 6/2005 | Cribier | 623/2.11 |
| 6,936,057 | B1 * | 8/2005 | Nobles | 606/194 |
| 6,945,957 | B2 * | 9/2005 | Freyman | 604/96.01 |
| 7,238,168 | B2 * | 7/2007 | Sirhan et al. | 604/96.01 |
| 7,374,560 | B2 * | 5/2008 | Ressemann et al. | 604/509 |
| 2001/0004699 | A1 * | 6/2001 | Gittings et al. | 606/153 |
| 2003/0018376 | A1 * | 1/2003 | Solar et al. | 623/1.11 |
| 2004/0138731 | A1 | 7/2004 | Johnson | |
| 2004/0199195 | A1 | 10/2004 | Dumontelle | |
| 2004/0210304 | A1 | 10/2004 | Seguin et al. | |
| 2004/0236418 | A1 | 11/2004 | Stevens | |
| 2004/0249435 | A1 | 12/2004 | Andreas et al. | |
| 2005/0015112 | A1 | 1/2005 | Cohn et al. | |
| 2005/0049696 | A1 | 3/2005 | Siess et al. | |
| 2005/0075724 | A1 * | 4/2005 | Svanidze et al. | 623/2.11 |
| 2005/0137690 | A1 | 6/2005 | Salahieh et al. | |
| 2005/0137696 | A1 | 6/2005 | Salahieh et al. | |
| 2005/0154443 | A1 * | 7/2005 | Linder et al. | 623/1.11 |
| 2005/0251251 | A1 * | 11/2005 | Cribier | 623/2.11 |
| 2006/0004439 | A1 * | 1/2006 | Spenser et al. | 623/1.23 |
| 2006/0074484 | A1 * | 4/2006 | Huber | 623/2.11 |
| 2006/0247570 | A1 * | 11/2006 | Pokorney | 604/9 |

\* cited by examiner

METHODS AND SYSTEMS FOR CARDIAC VALVE DELIVERY

REFERENCE TO RELATED APPLICATIONS

This application claims priority to Provisional Application Ser. No. 60/702,892 filed Jul. 27, 2005; Provisional Application Ser. No. 60/717,879 filed Sep. 16, 2005; Provisional Application Ser. No. 60/734,429 filed Nov. 8, 2005; Provisional Application Ser. No. 60/740,694 filed Nov. 29, 2005; and Provisional Application Ser. No. 60/762,909 filed Jan. 27, 2006; all of which are incorporated herein by reference

FIELD OF THE INVENTION

The present invention relates generally to methods and systems for cardiovascular surgery.

BACKGROUND OF THE INVENTION

Various surgical techniques may be used to repair a diseased or damaged heart valve, such as annuloplasty (contracting the valve annulus), quadrangular resection (narrowing the valve leaflets), commissurotomy (cutting the valve commissures to separate the valve leaflets), or decalcification of valve and annulus tissue. Alternatively, the diseased heart valve may be replaced by a prosthetic valve. Where replacement of a heart valve is indicated, the dysfunctional valve is typically removed and replaced with either a mechanical or tissue valve.

A number of different strategies have been used to repair or replace a defective heart valve. Open-heart valve repair or replacement surgery is a long and tedious procedure and involves a gross thoracotomy, usually in the form of a median sternotomy. In this procedure, a saw or other cutting instrument is used to cut the sternum longitudinally and the two opposing halves of the anterior or ventral portion of the rib cage are spread apart. A large opening into the thoracic cavity is thus created, through which the surgeon may directly visualize and operate upon the heart and other thoracic contents. The patient must typically be placed on cardiopulmonary bypass for the duration of the surgery.

Open-chest valve replacement surgery has the benefit of permitting the direct implantation of the replacement valve at its intended site. This method, however, is highly invasive and often results in significant trauma, risk of complications, as well as an extended hospitalization and painful recovery period for the patient.

Minimally invasive valve replacement procedures have emerged as an alternative to open-chest surgery. Wikipedia Encyclopedia defines a minimally invasive medical procedure as one that is carried out by entering the body through the skin or through a body cavity or anatomical opening, but with the smallest damage possible to these structures. Two types of minimally invasive valve procedures that have emerged are percutaneous valve procedures and trans-apical valve procedures. Percutaneous valve procedures pertain to making small incisions in the skin to allow direct access to peripheral vessels or body channels to insert catheters. Trans-apical valve procedures pertain to making a small incision in or near the apex of a heart to allow valve access. The distinction between percutaneous valve procedures and minimally invasive procedures is also highlighted in a recent position statement of the Society of Thoracic Surgeons (STS), the American Association for Thoracic Surgery (AATS), and the Society for Cardiovascular Angiography and Interventions (SCAI; Vassiliades Jr. TA, Block P C, Cohn L H, Adams D H, Borer J S, Feldman T, Holmes D R, Laskey W K, Lytle B W, Mack M F, Williams D O. The clinical development of percutaneous heart valve technology: a position statement by the Society of Thoracic Surgeons (STS), the American Association for Thoracic Surgery (AATS), and the Society for Cardiovascular Angiography and Interventions (SCAI). J Thorac Cardiovasc Surg. 2005; 129:970-6). Because minimally invasive approaches require smaller incisions, they generally allow for faster patient recovery with less pain and bodily trauma. This, in turn, reduces the medical costs and the overall disruption to the life of the patient.

The use of minimally invasive approaches, however, introduces new complexities to surgery. An inherent difficulty in the minimally invasive percutaneous approach is the limited space that is available within the vasculature. Unlike open heart surgery, percutaneous heart surgery offers a surgical field that is only as large as the diameter of the blood vessel used for access. Consequently, the introduction of tools and prosthetic devices becomes a great deal more complicated as compared to open-chest surgeries. The device must be dimensioned and configured to permit it to be introduced into the vasculature, maneuvered therethrough, and positioned at a desired location. This may involve passage through significant convolutions, at some distance from the initial point of introduction, before placement can be made at the intended site.

Andersen et al. describe a valve prosthesis implanted in a body channel by a way of catheterization in U.S. Pat. Nos. 5,411,442; 5,840,081; 6,168,614; and 6,582,462; and U.S. patent application Ser. No. 10/268,253, hereby incorporated by reference in their entirety. Catheters are hollow flexible tubes which can be passed inside blood vessels to the heart for diagnostic and treatment purposes. The delivery of catheter expanded valves through body channels such as that described by Andersen et al. is thus dependent on instruments of sufficiently small diameters, as well as adequate length and flexibility to navigate blood vessels.

Minimally invasive trans-apical valve replacement procedures have emerged as an alternative to both open-chest surgery and percutaneous valve surgeries. Bergheim et al. present improved methods and systems for cardiac valve delivery in U.S. Patent Application Ser. Nos. 60/702,892 and 10/831,770, hereby incorporated by reference in their entirety. Methods and systems for the repair, removal, and/or replacement of heart valves through the apex of the heart are described. This is an improvement over minimally invasive percutaneous approaches attempting insertion into the vasculature as the trans-apical approach is not limited by the space that is available within the vasculature. Trans-apical delivery is also closer to the heart than catheter-based procedures.

In-vivo studies have shown that catheter-based valve delivery instrumentation may not be well adapted for trans-apical procedures. When inserting balloon catheters, as described in U.S. Pat. No. 6,582,462 and U.S. patent application Ser. No. 10/831,770, it is difficult to steer the balloon and the valve into position resulting from the lack of rigidity and the inherent flexibility of catheters. This is especially true in minimally invasive trans-apical valve procedures. By their very nature, catheters are designed to be long, flexible and bendable to navigate long distances through the vasculature. Catheters are also frequently susceptible to twisting. As a result, catheters are typically thin and made of flexible materials such as plastics or polymers. Catheters are also designed to be disposed on guidewires to better direct the catheter to the correct location. Even so, it is difficult to steadily and accurately deliver tools and devices over long distances. This is especially true in high flow situations such as a beating heart and in places offering the catheters a substantial amount of space to move within. Correct and accurate placement of a heart valve requires both accurate longitudinal positioning as well as rotational positioning. It is important to correctly place the valve as much as possible into a position that mimics that of the native valve to maximize durability and function. It is also important to prevent placement of the valve in a manner that blocks the left and right coronary outflow (as in the case of the aortic valve). There is hence a need to accurately maneuver and steer the valve during implantation. There is also a need for a device that is more suitable for delivering valves during trans-apical procedures.

During balloon-inflation of a flexible leaflet valve, such as a stented tissue valve, it is desired that the valve remain on the balloon until it is firmly positioned at the site of implantation. In the case of balloon-expandable valves, there is hence a need for devices designed to make sure the valve stays on the balloon during inflation.

Bergheim further presents methods and assemblies for distal embolic protection in U.S. patent application Ser. No. 10/938,410, hereby incorporated by reference in its entirety. Here, Bergheim describes distal embolic protection assemblies for use during trans-apical valve surgery. In order to accommodate a distal embolic protection assembly alongside other valve insertion and replacement devices, it is important that the distal embolic protection assembly collapses down to a substantially small diameter to minimize the space it occupies Macoviak et al. present a filter catheter used to capture potential emboli within the aorta during heart surgery and cardiopulmonary bypass in U.S. patent application Ser. No. 10/108,245, hereby incorporated by reference in its entirety. The filters described by Macoviak are adapted for use during cardiopulmonary bypass, and not during beating heart surgery. The filters described by Macoviak are also intended to be inserted through the femoral artery and further fail to incorporate a temporary valve, useful for capturing large amounts of debris while performing beating heart surgeries. There is hence a need for a filter system better suited for percutaneous and trans-apical valve surgeries.

Accordingly, while open-heart surgery produces beneficial results for many patients, numerous others who might benefit from such surgery are unable or unwilling to undergo the trauma and risks of current techniques. Therefore, what is needed are methods and devices for performing heart valve repair and replacement as well as other procedures within the heart and great vessels of the heart that provide greater ease of access to the heart valves than the current minimally invasive techniques, while at the same time reducing the trauma, risks, recovery time and pain that accompany more invasive techniques.

SUMMARY OF THE INVENTION

The present invention provides methods and systems for performing cardiovascular surgery, wherein access to the heart or great vessels is provided through the heart muscle. In preferred embodiments, access is provided through the apical area of the heart. The apical area of the heart is generally the blunt rounded inferior extremity of the heart formed by the left and right ventricles. In normal healthy humans, it generally lies behind the fifth left intercostal space from the midsternal line.

The unique anatomical structure of the apical area permits the introduction of various surgical devices and tools into the heart without significant disruption of the natural mechanical and electrical heart function. Because the methods and systems of the present invention permit direct access to the heart and great vessels through the apex, they are not limited by the size constraints which are presented by minimally invasive percutaneous valve surgeries. While access to the heart through peripheral (e.g. femoral, jugular, etc) vessels in percutaneous methods are limited to the diameter of the vessel (approximately 1 to 8 mm), access to the heart through the apical area is significantly larger (approximately 1 to 25 mm or more). Thus, apical access to the heart permits greater flexibility with respect to the types of devices and surgical methods that may be performed in the heart and great vessels.

Accordingly, it is one object of this invention to provide methods and devices for the repair, removal, and/or replacement of valves or their valve function by access through the heart muscle, particularly through the apical area of the heart. It should be noted that while reference is made herein of trans-apical procedures, it is intended for such procedures to encompass access to the heart through any wall thereof, and not to be limited to access through the apex only. While the apical area is particularly well suited for the purposes of the present invention, for certain applications, it may be desirable to access the heart at different locations, all of which are within the scope of the present invention.

In one embodiment of the present invention, a method for delivering a prosthesis to a target site in or near a heart is provided. The method comprises introducing a delivery system into the heart, preferably at or near the apex of the heart, wherein a prosthesis is disposed on the delivery member attached to the delivery system, advancing the prosthesis to the target site, and disengaging the prosthesis from the delivery member at the target site for implantation. In another embodiment of the current invention, a method for delivering a prosthesis to a pre-existing man-made valve within or near a heart is provided.

The present invention also provides an implant system for delivering a prosthesis to a target site in or near a heart. In one embodiment of the present invention, the implant system comprises a delivery system, an access system, and a prosthesis. In one embodiment of the present invention, the access system is a trocar, cannula, or other suitable device to penetrate the heart, preferably at or near the apex of the heart; and the delivery system is substantially rigid and movably disposed within the trocar, wherein a prosthetic valve is disposed on the delivery member attached to the delivery system. In one embodiment of the present invention, the delivery system is termed a Scapus™ system. The term "Scapus™" denotes a slender or elongated rod shaped support structure that is substantially rigid. The term substantially rigid implies structural stability to withstand fluid pressures and other forces without unintended deformation. On the other hand, the Scapus™ may encompass junctions or other means of controlled bending to allow for directional control by the operator at predetermined points along the length of the Scapus™. In one embodiment of the current invention, the delivery system comprises a Scapus™ and a delivery member.

The delivery system may be used to deliver a variety of prosthetic heart valves, including stented and stentless tissue valves. In one embodiment of the present invention, the delivery member comprises a mechanical or inflatable expanding member to facilitate implantation of the prosthetic valve at the target site. In another embodiment of the present invention, the delivery member is a balloon. In another embodiment of the present invention, the delivery member is a device used to expand folded valves. In yet another embodiment of the present invention, the delivery member may comprise an inflatable balloon member, whose distal and proximal ends have substantially larger cross-sectional areas than the portion of the balloon covered by the prosthesis, to prevent prosthesis migration. In a further embodiment of the present invention, the delivery system may comprise a duct or perfusion tube to allow blood flow through the delivery member during the procedure.

It is a further object of the current invention to provide systems and methods for converting a catheter into a Scapus™ delivery system. In one embodiment of the current invention, a substantially thin, stiff guide-stick is inserted into the catheter to give it similar characteristics as a Scapus™. In another embodiment of the current invention, a substantially thin, stiff guide-sleeve slides on the outside of a catheter to give it similar characteristics as a Scapus™.

The delivery systems described herein may be used to deliver prosthetic valves to all four valves of the heart including the aortic valve, mitral valve, tricuspid valve, and pulmonary valve. Different anatomical features for the different heart valves (bicuspid vs. tricuspid valves) may call for different design heart valves. Therefore, in one embodiment of the present invention, the prostheses are designed to match the anatomy of the target valve position. In another embodiment of the current invention, the prosthesis is composed of a tissue valve mounted in a stent.

One group of patients that will benefit from a trans-apical procedure is patients who have had previous valve replacements, and where replacement valves are failing. Rather than performing yet another open-chest procedure, many of these patients may be candidates for trans-apical valve replacements. This is especially the case for older patients who may not tolerate the stress of a new open-chest procedure. For these patients, who have a failing valve, one may seat the new trans-apical delivered prosthesis inside the failing valve. Therefore, in one embodiment of the present invention, the new prosthesis matches the configuration of the failing valve. Some patients who have had previous valve replacements, and whose valve replacement valves are failing may also be candidates for percutaneous valve procedures. For these patients, who have a failing valve, one may seat the new percutaneously delivered prosthesis inside the failing valve.

The present invention also provides for devices and methods for providing distal embolic protection and a temporary valve. In one embodiment of the present invention, the distal embolic protection system provides a filter member for trapping embolic material that concurrently functions as a temporary valve. The filter and temporary valve assembly prevents flush back of embolic material and debris, while still allowing fluid flow into the filter during surgery. The valve-filter combination may be compressed and expanded to allow entry into small blood vessels or other body cavities. In one embodiment of the present invention, the filter assembly is implanted in the heart or great vessel of the heart, downstream from the surgical site.

In one embodiment of the present invention, a valvuloplasty balloon is inflated to increase the effective orifice area of a heart valve. In another embodiment of the present invention, the valvuloplasty balloon slides over the guide wire or actuation sleeve connected to the distal embolic protection device.

Since a transapical procedure does not provide direct line of sight, sufficient imaging of the heart, valves, and other structures is important to provide diagnostics, guidance and feed-back during the procedure. A Scapus™ delivery system may be of a larger diameter than that of a catheter and is thus better suited for containing imaging transducers. Thus in one embodiment of the present invention, an imaging transducer is placed onto the delivery system. In another embodiment of the present invention, an external imaging transducer may be provided to view the operating field. Imaging systems may be used at any time or throughout the duration of the surgery. Imaging systems are well-known to those skilled in the art and include transesophageal echo, transthoracic echo, intravascular ultrasound imaging (IVUS), intracardiac echo (ICE), or an injectable dye that is radiopaque. Cinefluoroscopy may also be utilized.

In another embodiment of the present invention, a positioning balloon is used to help position the Scapus™ correctly such that the new prosthesis (or alternatively other tools) land in the proper location.

In yet another embodiment of the present invention, the method and system may further comprise means to remove at least a portion of the patient's heart valve by a cutting tool that is disposed on the delivery system.

In a further embodiment of the present invention, the methods and devices of the present invention may be adapted to provide a valve decalcification system, wherein the delivery system is capable of providing a dissolution solution to the treatment site by access through the apical area of the heart. The delivery system may be a catheter or a Scapus™ that is configured with means to both introduce and remove the dissolution solution to the treatment site. The delivery system may also provide means for isolating the treatment site to prevent the dissolution solution from entering into the patient's circulatory system. Such means for isolating the treatment site may include a barrier, such as a dual balloon system on the catheter that inflates on both sides of the treatment site.

The present invention provides methods and systems for creating a calcified animal model for use in the development and testing of cardiac valves.

Although many of the above embodiments are referenced with respect to the aortic valve in the heart, the current invention may also be utilized for procedures related to the mitral valve, tricuspid valve, and the pulmonary valve.

The above aspects and other objects, features and advantages of the present invention will become apparent to those skilled in the art from the following description of the preferred embodiments taken together with the accompanying figures.

DETAILED DESCRIPTION OF THE PREFERRED EMBODIMENTS

FIGS. 1 through 16 show embodiments of the methods and systems of the present invention for the repair, removal, and/or delivery of prosthetic valves, and also for providing distal embolic protection and a temporary valve during cardiovascular procedures.

Valve Delivery Method and Implantation System

Figure 1:
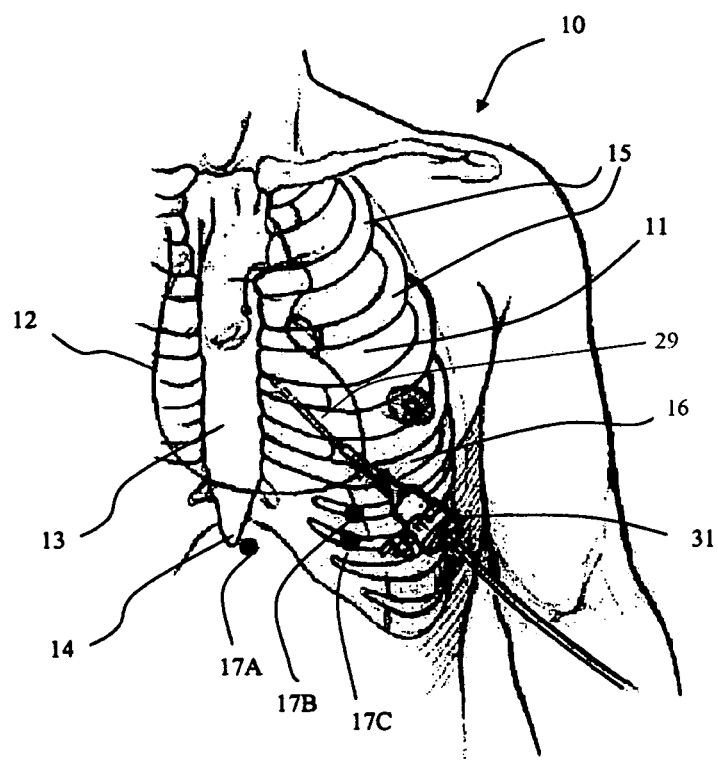
FIG. 1 is a partial front view of a patient's chest showing a prosthesis introduced into the apex of the heart through the fifth intercostal space using an implant system.

FIG. 1 is a partial front view of the chest 11 of a patient 10 and shows the position of a surgical tool 29 in relation to other anatomical landmarks, such as the sternum 13, xiphoid 14, ribs 15, and heart 12. A surgical tool 29 is depicted as entering the body cavity through the fifth intercostal space 16 and through the apex of the heart 12. The surgical tool 29 is seen inserted through an access system 31. The surgical tool 29 may contain devices or systems used for surgical procedures in or on the heart or the greater vessels of the heart. In one embodiment of the current invention, the surgical tool 29 is a delivery system. In another embodiment of the current invention, the surgical tool 29 may be a distal embolic protection device. The surgical tool 29 may enter the body cavity through various other locations 17A, 17B and 17C in the chest 11. In another embodiment of the current invention, the surgical tool 29 may be a plurality of devices. In one embodiment of the current invention, the surgical tool 29 is both a delivery system and a distal embolic protection system.

In one embodiment of the present invention, the implant system comprises an access system, delivery system, and a prosthesis. In one embodiment of the current invention, the prosthesis is a heart valve prosthesis. In another embodiment of the current invention, the access system 31 is a trocar, cannula, or other suitable device for penetrating the apex 18 of the heart 12. In another embodiment of the current invention, the delivery system is composed of a delivery member, wherein the prosthetic valve is disposed on the delivery member. In another embodiment of the current invention, the delivery system is substantially rigid. In yet another embodiment of the current invention, the substantially rigid support structure of the delivery system is called a Scapus™. Inherent in its definition, the term Scapus™ implies a rigid support structure with other devices, tools, and assemblies attached to it. In one embodiment of the current invention, the delivery member of the delivery system is attached to the Scapus™.

The delivery system described in the current invention presents major advances over the use of catheters as delivery systems for procedures in close vicinity of the heart. By their very nature, catheters are designed to be flexible to navigate long distances. Catheters must also be able to twist and bend to move through bends in the vasculature, such as those encountered in percutaneous procedures. Catheters are also designed to be disposed on guidewires to better direct the catheter to the correct location. Even with the use of guidewires, it is difficult to steadily and accurately deliver tools and devices over long distances. This is especially true in high flow situations such as a beating heart procedure. Correct and accurate placement of a heart valve requires both accurate longitudinal positioning as well as rotational positioning. It is important to correctly place the valve as much as possible into a position that mimics that of the native valve to maximize durability and function. It is also important to prevent placement of the valve in a manner that blocks the left and right coronary outflow (as in the case of the aortic valve).

Accurate delivery of cardiac valves in trans-apical procedures requires accurate and precise longitudinal and rotational positioning. Longitudinal positioning implies positioning along the length of the aorta. Rotational positioning implies rotational positioning around the lengthwise direction of the aorta. The route from the apex of the heart to all four cardiac valves is also a substantially straight line, meaning that the maneuvering features such as bending, twisting, and torsion of a catheter are not typically desired. In fact, the inherent maneuvering features of a catheter are disadvantageous in this procedure as it allows bending and torsion and is not able to hold the delivery member in place during valve implantation. The blood flow and pressure inherent in a beating heart procedure in combination with a catheter delivery system therefore does not allow accurate and precise delivery of prosthetic valves.

An object of the present invention is therefore to provide a delivery system that is substantially rigid to resist any unintended bending and torsion. A Scapus™, in contrast to a catheter, provides sufficient rigidity to accurately and precisely deliver a prosthesis during a beating heart procedure. A Scapus™ delivery system is designed not twist or bend unless intended by the operator. The Scapus™ of the present invention can incorporate junctions or other means of bending at predetermined points to allow the operator to adjust the direction or angle of the delivery path in a controlled fashion.

In one embodiment of the present invention, the Scapus™ provides rigid support between the operator and the distal portion of the delivery system located in the heart. In contrast to catheter delivery systems, a Scapus™ delivery system may incorporate a larger cross-sectional area since access through the heart walls provides a larger access port diameter (in some instances up to 25 mm or more) compared with the vasculature (0 to 8 mm or less).

In one embodiment of the current invention, the Scapus™ is made of a material that substantially resists bending and torsion. One example of such a material is stainless steel or substantially strong polymer plastics.

In one embodiment of the current invention, the Scapus™ is a solid rod. In yet another embodiment of the current invention, the Scapus™ is a hollow rod. A Scapus™ may contain one or more lumens for moving fluid. A Scapus™ may also contain actuating members such as rods, wires, guidewires, or catheters. A Scapus™ may also conduct or transmit electricity or electrical signals and may also transmit light or light signals. A Scapus™ may also transmit radiation or other forms of energy such as ultrasound, ultraviolet light, infrared light, or gamma rays.

A catheter used for percutaneous valve procedures are typically longer than 50 cm to navigate through the vasculature. By contrast, the Scapus™ length can be less than 50 cm. In preferred embodiments of the present invention, the length of the Scapus™ can be about 15-30 cm in total, of which about 10 cm may be inserted into heart, and the remaining length left outside.

The methods and systems of the present invention may be used to implant a variety of heart valve prosthesis known in the art, including stented and stentless tissue valves. The methods and systems of the present invention may also be used to implant a variety of stents. In one embodiment of the present invention, the prosthetic delivery member is located towards the distal end of the delivery system. Stented valves may be expandable by mechanical or balloon expansion devices, or they may be self-expanding. Self-expanding stents may be constructed from elastic materials such as memory shaped metal alloys. An example of a memory shaped metal alloy is that of Nitinol. The valves are expanded using the valve expansion member located on the delivery system. In one embodiment of the present invention, the delivery member is a mechanically actuated device used to expand stented valves. In another embodiment of the current invention, the delivery member is a balloon expansion device. In another embodiment of the present invention, the delivery member is a balloon used for radial expansion. In yet another embodiment of the current invention, the delivery member contains a self-expandable heart valve. There are numerous methods and systems for releasing a self-expandable expandable heart valve. One example is U.S. Pat. No. 6,682,558, hereby incorporated by reference in its entirety.

Stented valves may also be expandable by unfolding the valve. The valve may be unfolded by using a balloon or mechanical expansion device. Alternatively, the folded valves may be self-expanding. Self-expanding stents may be constructed from elastic materials such as memory shaped alloys. The valves are expanded using the valve expansion member located on the delivery system. In one embodiment of the present invention, the delivery member is a mechanically actuated device used to expand stented valves that have been folded. In another embodiment of the current invention, the delivery member is a balloon expansion device. In such an embodiment, the balloon and stented valve have been folded together. When inflated, the balloon and stented valve return to their original shape. When unfolding a stented valve using a mechanical expansion device or a balloon, the stent making up the stented valve is typically made from a non-memory shaped alloy. Examples of suitable materials include stainless steel, polymers, plastics, and non-memory shaped metals. In another embodiment of the present invention, the delivery member is used to unfold stented valves made from memory shaped alloys. In one embodiment of the present invention, the delivery member consists of a hollow tube in which the stented valve is placed into and a plate or actuating mechanism just proximal to the valve used to push out the valve out of the hollow tube.

Alternatively, the methods and devices of the present invention may also be used to implant a stentless prosthetic heart valve. In one embodiment of the present invention, the delivery member is adapted to position the tissue valve at the target site and the deliver member further comprises a means to suture or staple the tissue valve to the valve annulus.

Examples of suitable prosthetic valves are disclosed in the following commonly owned patents: U.S. Pat. Nos. 6,682,559; 5,480,424; 5,713,950; 5,824,063; 6,092,529; 6,270,526; 6,673,109; 6,719,787; 6,719,788; and 6,719,789, incorporated herein by reference. Examples of other valve assemblies suitable for use in connection with the present invention are described in U.S. Pat. Nos. 5,411,552; 6,458,153; 6,461,382; and 6,582,462, incorporated herein by reference. Yet another valve suitable for use in connection with the present invention is disclosed in U.S. patent application Ser. No. 10/680,071, hereby incorporated for reference in its entirety.

Figure 2:
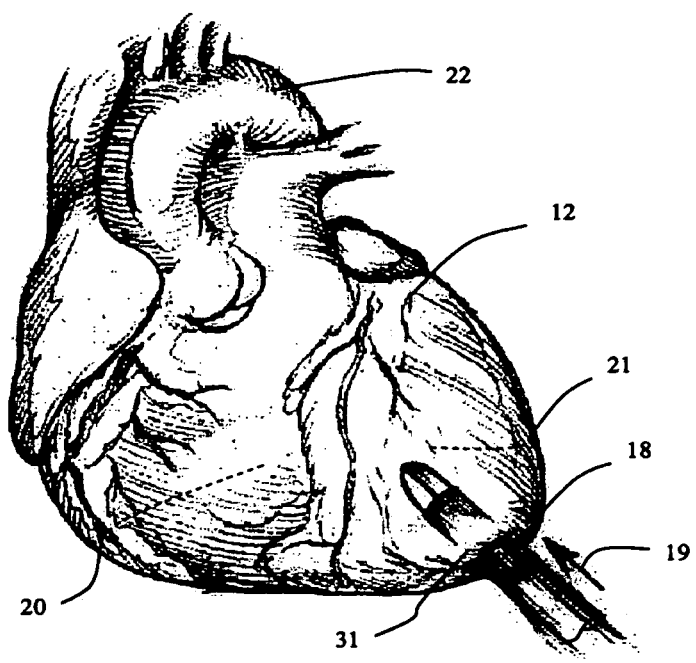
FIG. 2 depicts a trocar penetrating the apex of the heart and into the left ventricle.

Access systems suitable for use in connection with the present invention typically comprise a hollow lumen and a first and second ends. In one embodiment of the present invention, the access system 31 is a trocar. The first end comprises a means for penetrating the heart tissue and the second end comprises a port through which the valve delivery system may be introduced into the hollow lumen of the trocar and into the heart. FIG. 2 depicts an access system 31 penetrating through the apex 18 of the heart 12. The moving direction of the access system 31 is indicated by the arrow 19. The access system 31 can enter either the right ventricle 20 or the left ventricle 21. To access the aortic or mitral valve, the trocar 31 would preferably pass through the left ventricle 21. This yields direct access to the aortic or mitral valve. To access the pulmonary or tricuspid valve, the trocar 31 would preferably pass through the right ventricle 20.

In another embodiment of the present invention, the access system 31 further comprises a valve disposed within its lumen. The valve is designed to reduce significant backflow of blood out of the heart 12 after the access system 31 is inserted into the beating heart 12, while at the same time permitting the introduction of the delivery member and other surgical devices in through the access system 31. Other suitable access systems 31 and devices are well known in the art and are disclosed in U.S. Pat. Nos. 5,972,030; 6,269,819; 6,461,366; 6,478,806; and 6,613,063, incorporated herein by reference.

In one embodiment of the present invention, the operator places a pursestring suture on the apex 18 of the heart 12 to create a seal around the access system 31. Another embodiment of the present invention allows the use of the Scapus™ delivery system without an access system 31. It is contemplated that the physician becomes familiar with the advantages of the present invention and thus may find it unnecessary to use a trocar. In the latter case, the distal embolic protection system and the delivery system is placed directly through an incision in the apex 18 or other area of the heart wall. In another embodiment of the current invention, a delivery sleeve or delivery sheath is placed on the delivery system.

In one embodiment of the present invention, an off-the-shelf valvuloplasty balloon catheter is introduced through the access system 31 into the apex 18 of the heart 12, positioning the balloon of the catheter within the valve and valve annulus. Valvuloplasty balloons are well known to anyone skilled in the art. Once the balloon is placed within the valve, it may be inflated to widen a stiff or narrowed heart valve (stenotic heart valve) improving blood flow through the heart and to the rest of the body. Previous methods for performing valvuloplasty required the insertion of a catheter typically through the femoral artery or femoral vein which is then guided through the heart and positioned through the diseased heart valve. The methods and devices of this present invention, however, provide a more direct route to the valve to be treated.

In another embodiment of the present invention, the delivery member of the delivery system described in the current invention is used to valvuloplasty the diseased valve. In such an embodiment, the delivery member of the delivery system is first guided to the diseased heart valve and positioned within the valve and valve annulus. After expanding the valve orifice, the delivery system is withdrawn from the access system 31 and a new prosthetic valve is placed onto the valve delivery system. The valve delivery system is further introduced through the access system 31 and the delivery member moved into position within the valve orifice to expand and implant the valve.

Figure 3:
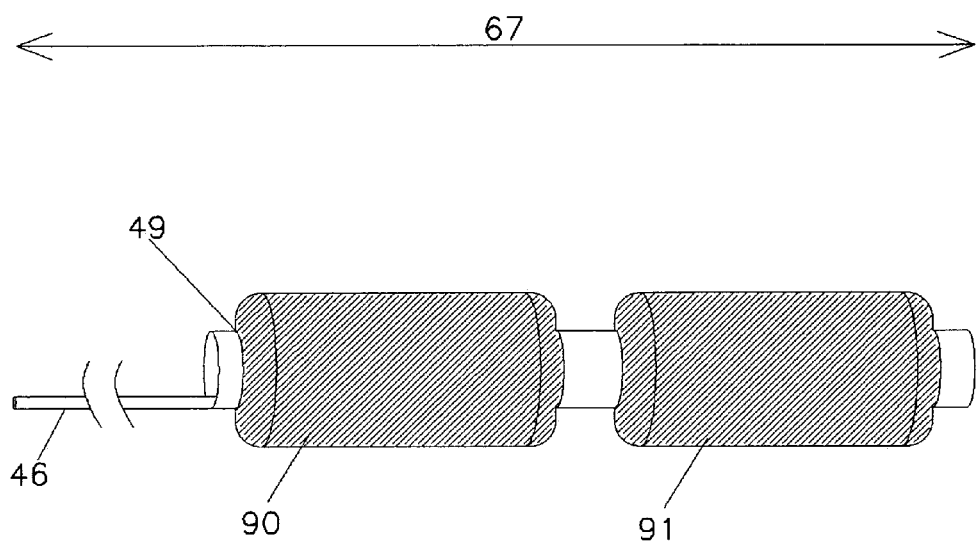
FIG. 3 shows two independent balloon delivery members contained on the Scapus™ delivery system for providing both valvuloplasty and valve delivery.

In yet another embodiment of the present invention, two independent delivery members are contained on the delivery system. Such a system is shown in FIG. 3. Here, the delivery system 67 includes a Scapus™ 46, a perfusion tube 49, and two independently operated balloon delivery members 90 and 91. Such a configuration allows the delivery system 67 to be used both for valvuloplasty and valve delivery. In such an embodiment, the most distal delivery member 91 is first guided to the diseased heart valve and positioned within the valve and valve annulus. After expanding the valve orifice, the delivery system 67 is moved such that the second most proximal delivery member 90, onto which the prosthetic valve is placed, is moved within the valve and valve annulus to expand and implant the valve. In a further embodiment of the present invention, no perfusion tube 49 is present and the balloons 90 and 91 are in intimate contact with the Scapus™ 46. The use of two balloons 90 and 91 as shown in FIG. 3 is not only practical in trans-apical valve procedures, but also in percutaneous valve procedures. Thus, in one embodiment of the present invention, the Scapus™ 46 shown in FIG. 3 is a catheter. In a further embodiment of the foregoing embodiment, the catheter is a multilumen catheter.

Balloon Systems and Implantation Methods Thereof

Regardless of the type of valve delivery member utilized, it is important that the prosthetic valve remain securely attached to the delivery member during implantation. This is especially true if the operator accidentally or intentionally lowers the pressure in the balloon (via a syringe, etc). Thus, the present invention further provides balloons that are shaped such that the distal and proximal ends of the balloon, not covered by the prosthetic valve, are larger in area, and thus prevents migration of the valve. Such a balloon may take the shape of a "dog-bone".

Figure 4:
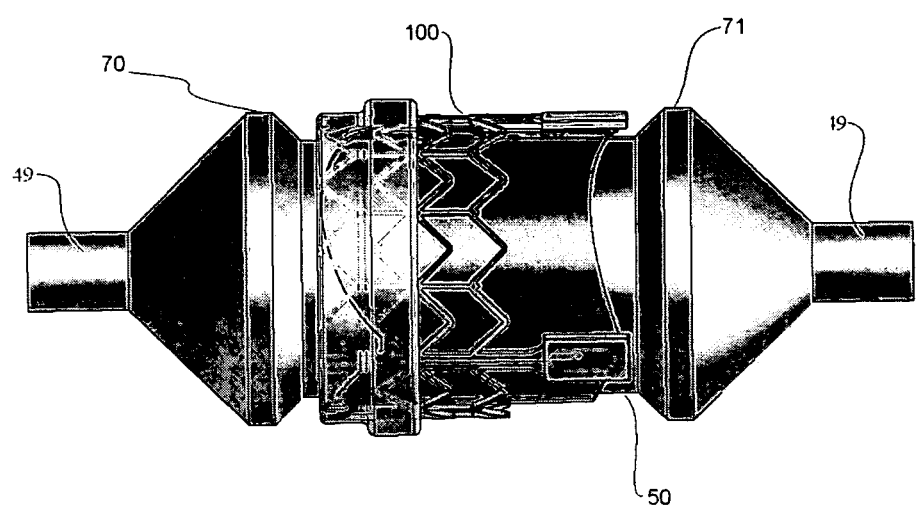
FIG. 4 shows a prosthetic valve disposed onto a "dog-bone" shaped balloon.

FIG. 4 shows a balloon 50 delivery member whose proximal end 70 and distal end 71 have a larger cross sectional area than the middle portion of the balloon in intimate contact with the prosthetic valve 100. FIG. 4 also shows a perfusion tube 49 extending through the balloon from the proximal end 70 to the distal end 71 of the balloon delivery member 50 allowing fluid to flow through the length of the balloon delivery member 50. In one embodiment of the present invention, the balloon delivery member 50 does not contain a perfusion tube 49. The orientation of the prosthetic valve 100 on the balloon delivery member 50 shown in FIG. 4 in relation to the proximal end 70 and distal end 71 of the balloon delivery member 50 depends on the implantation method in relation to the blood flow direction through the native valve. The orientation shown in FIG. 4 is preferred for apical implantation. In another embodiment of the present invention, the prosthetic valve 100 is oriented the opposite direction on the balloon delivery member 50.

In one embodiment of the present invention, the distal end 71 and proximal end 70 of the balloon delivery member 50 has a material coating that has a larger coefficient of friction with the prosthetic valve as opposed to the middle portion of the balloon delivery member 50. In the case of a balloon delivery member 50, an example of a material that has a larger coefficient of friction with a prosthetic valve as compared to the balloon is cloth. Increasing the roughness in the plastic making up the balloon will also increase the coefficient of friction with the prosthetic valve.

The "dog-bone" shape balloon delivery member 50 described herein is not limited to Scapus™ delivery systems. Such balloons can be utilized in any type of stent delivery. Thus, in one embodiment of the present invention, the "dog-bone" balloon delivery member 50 described herein may be utilized in any type of stent or prosthetic valve delivery system. In one embodiment of the present invention, the "dog-bone" balloon delivery member 50 is utilized on a catheter valve delivery system, such as those used for percutaneous valve delivery.

Delivery System and Methods

Figure 5:
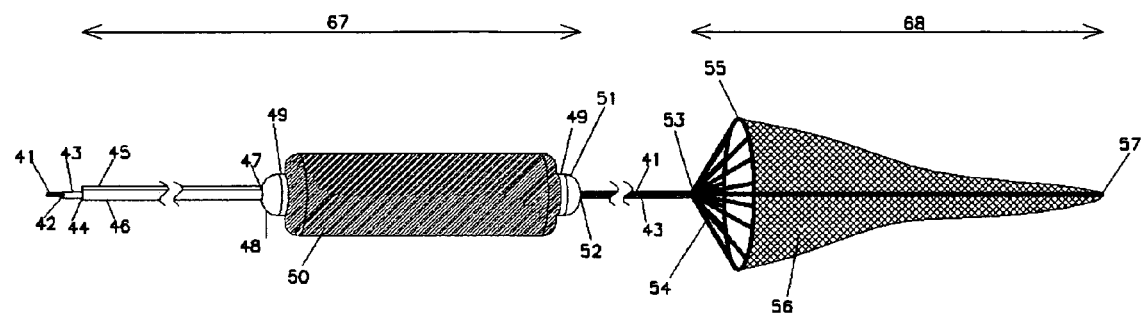
FIG. 5 shows a Scapus™ delivery system and a distal embolic protection assembly.

FIG. 5 depicts a delivery system 67 consisting of a Scapus™ 46, balloon inflation tube 45, proximal balloon delivery member connector 48, distal balloon member connector 51, perfusion tube 49, and a balloon delivery member 50. In a preferred embodiment of the present invention, the proximal balloon delivery member connector 48 and the distal balloon delivery member connector 51 have a hole or a plurality of holes allowing blood to flow through the perfusion tube 49 and hence through the balloon delivery member 50. In another preferred embodiment, the Scapus™ 46 comprises a substantially rigid solid rod. In one embodiment of the present invention, the Scapus™ 46 and the balloon inflation tube 45 are glued or fused together at a plurality of points along the extent of the Scapus™ 46. In another embodiment of the present invention, the Scapus™ 46 contains one or more inside lumens. In yet another embodiment of the current invention, the balloon inflation tube 45 is disposed within the Scapus™ 46. In another embodiment of the current invention, the balloon inflation tube 45 is one of the internal lumens of the Scapus™ 46. In yet another embodiment of the current invention, the Scapus™ 46 may be bent in a controlled fashion, using a bending force. As used herein, bending force here means bending moment that can be created by the use of the operators' hands. The Scapus™ 46 cannot be bent by the much smaller forces imposed by the blood flow and the beating heart. The Scapus™ 46 may further incorporate junctions or other bending means that allow for operator-controlled bending of the Scapus™ 46 at predetermined points.

FIG. 5 also shows a distal embolic protection assembly 68. The distal embolic protection assembly consists of a frame 55 and a porous bags 56. In one embodiment of the present invention, the distal inlet portion of the filter mouth 53 includes a temporary valve.

In one embodiment of the present invention, the delivery system 67 is inserted through the trocar 31 into the left ventricle 21 and advanced towards the native aortic valve of the heart 12. The delivery system 67 may be composed of a substantially rigid Scapus™ 46 and a delivery member. The heart valve prosthesis 100 is disposed around the balloon delivery member 50 and delivered to the target site for implantation. The length of balloon delivery members 50 suitable for the purposes of the present invention will depend on the height of the prosthetic valve 100 to be implanted.

Figure 6:
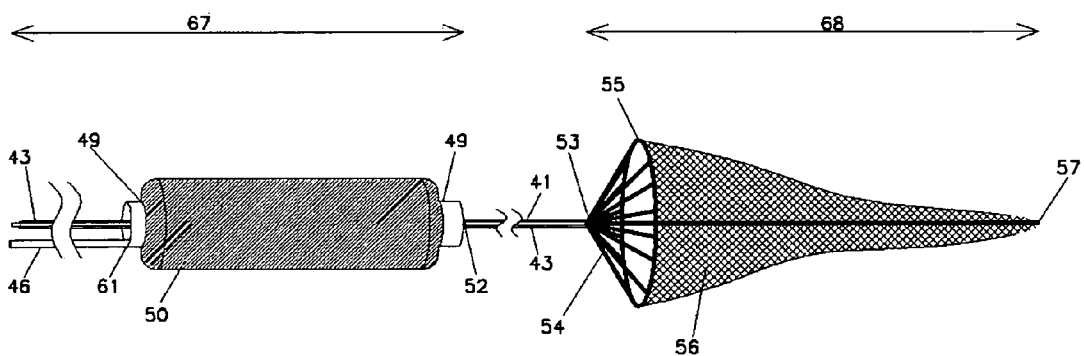
FIG. 6 shows a Scapus™ delivery system and a distal embolic protection assembly.

FIG. 6 shows a delivery system 67 comprising a perfusion tube 49, balloon delivery member 50, and a Scapus™ 46. Here, the Scapus™ 46 is rigidly attached to the perfusion tube 49. In one embodiment of the current invention, the Scapus™ 46 has a lumen that extends to the balloon delivery member 50 and serves to inflate and deflate the balloon. The actuation sleeve 43 and guidewire 41 is loosely disposed within the perfusion tube 49.

In one embodiment of the present invention, the distal embolic protection assembly 68, actuation sleeve 43 and guidewire 41 within activation sleeve 43 is movably disposed within the Scapus™ 46 of the delivery system 67 and balloon delivery member 50 shown in FIG. 6. In yet a further embodiment of the present invention, the distal embolic protection assembly 68 may be collapsed and moved through the Scapus™ 46 and balloon delivery member 50. In one embodiment of the present invention, the delivery system shown in FIG. 6 is inserted through the trocar 31 in two steps: first the distal embolic protection assembly 68; second the delivery system 67 and balloon delivery member 50. After having introduced the trocar 31 through the apex 18 of the heart 12, the distal embolic protection assembly 68 is moved in a collapsed configuration through the trocar 31 and the left ventricle 21 and placed downstream from the aortic valve. Once the distal embolic protection assembly 68 is in position, the distal embolic protection assembly 68 is expanded to seal the inside circumference of the aorta. Expansion takes place by moving the actuation sleeve 43 relative to the guidewire 41. All circulation through the aorta will hence have to be filtered in the porous bag 56 of the distal embolic protection assembly 68. The guidewire 41 and actuation sleeve 43 extends from the proximal side of the distal embolic protection assembly 68 to the outside of the body 10 and is accessible to the operator. In one embodiment of the present invention, the actuation sleeve 43 may also be used as a guidewire to move the Scapus™ 46 into position. Thus in one embodiment of the current invention, the Scapus™ delivery system may be loosely disposed on a guidewire 41. In yet another embodiment of the present invention, the perfusion tube 49 functions as the actuation sleeve 43 to open and collapse the distal embolic protection catheter.

Figure 7:
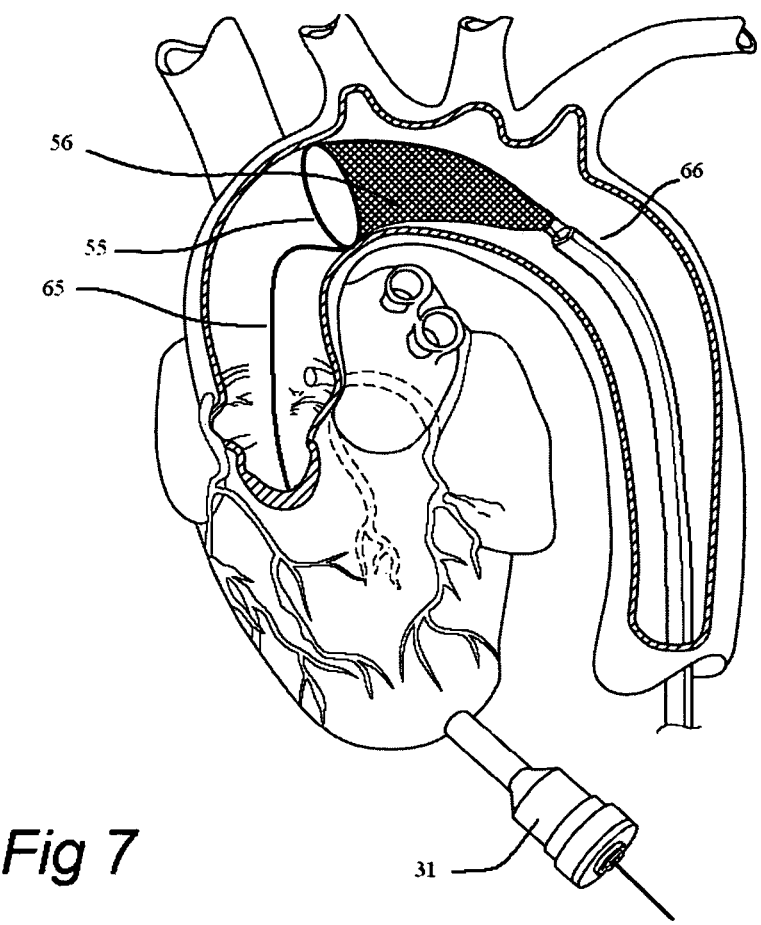
FIG. 7 shows the distal embolic protection system positioned in the aorta and inserted through the femoral artery.

Distal embolic protection assemblies 68 may be introduced through the apex 18 of the heart 12. Such embodiments are summarized in co owned U.S. application Ser. No. 10/938, 410, hereby incorporated by reference in its entirety. Distal embolic protection assemblies 68 may also be inserted through arteries such as the femoral artery such as those disclosed by Macoviak, et al in U.S. application Ser. No. 10/108,245, hereby incorporated for reference in its entirety. In another embodiment of the present invention, the distal embolic protection filter assembly 68 is introduced through the femoral artery and moved to the aortic arch, positioned just downstream of the aortic valve as shown in FIG. 7. A delivery sheath 66 is used to collapse the filter assembly composed of the filter frame 55 and the porous bag 56. In a further embodiment of the current invention, a guidewire 65 is attached to the frame 55 on the proximal side of the filter assembly 68 and continues through the aortic valve and out through the trocar 31 and out through the body 10. The guidewire 65 may be used for guiding the delivery system 67 into position through the trocar 31 and the apex 18 of the heart. The way the guidewire 65 is attached to the mouth of the filter 55 is for illustrational purposes only. Anyone skilled in the art will appreciate there are many different ways of attaching a guidewire to the mouth 55 of the filter and different opening and closing mechanism for the filter. Other aortic filter systems described in prior art for femoral artery insertion may also be adapted for this procedure.

In one embodiment of the current invention, the delivery sheath 66 shown in FIG. 7 is a Scapus™ 46 delivery system. The Scapus™ 46 delivery system may slide across the guidewire. The porous bag 56 may also be inserted and removed through the delivery system.

Once the distal embolic protection assembly 68 has been placed into position, the Scapus™ 46 of the delivery system 67 slides over the actuation sleeve 43 through the apex 18 of the heart 12. In one embodiment of the present invention, the delivery system 67 slides over the guidewire 41 or 65, depending on the configuration of the distal embolic protection assembly. The balloon delivery member 50 is positioned in the aorta and within the aortic valve and aortic valve annulus. In one embodiment of the present invention, the distal embolic protection system 68 and valve delivery system 67 is inserted through the apex 18 together.

A collapsed replacement heart valve prosthesis 100 is disposed on the balloon delivery member 50. The delivery system 67 with the attached replacement prosthetic valve slides over the actuation sleeve and is introduced into the port of the access system 31 and through the apex 18 of the heart 12. The balloon delivery member 50 with the attached heart valve prosthesis 100 is positioned in the aorta and within the aortic valve and aortic valve annulus. The balloon delivery member 50 is expanded by moving fluid through the balloon inflation tube 45. The balloon inflation tube 45 connects fluid to the balloon delivery member 50. In one embodiment of the present invention, the device used to move fluid through the balloon inflation tube 45 is a syringe. The balloon delivery member 50 expands in a radial direction when filled with fluid through the balloon inflation tube 45 causing the replacement prosthetic valve 100 to exert force against the existing valvular leaflets and the walls of the vessel.

In one embodiment of the present invention, the valve replacement procedure described herein is done more than once. A repeat procedure may, for example, be performed in patients who cannot tolerate an open chest surgery.

Once the heart valve prosthesis 100 is implanted, the balloon delivery member 50 is deflated and the valve delivery system 67 is withdrawn from the body. The distal embolic protection assembly 68 is further withdrawn from the body 10. In one embodiment of the present invention, the distal embolic protection assembly 68 and the valve delivery system 67 are withdrawn from the body together. In one embodiment of the present invention, a distal embolic protection assembly 68 is not utilized. In yet another embodiment of the present invention, the distal embolic protection assembly 68 is left in the body for some time (up to 7 days) after the operation to make sure that the porous bag 56 of the distal embolic filter assembly 67 has collected all the debris.

Figure 8:
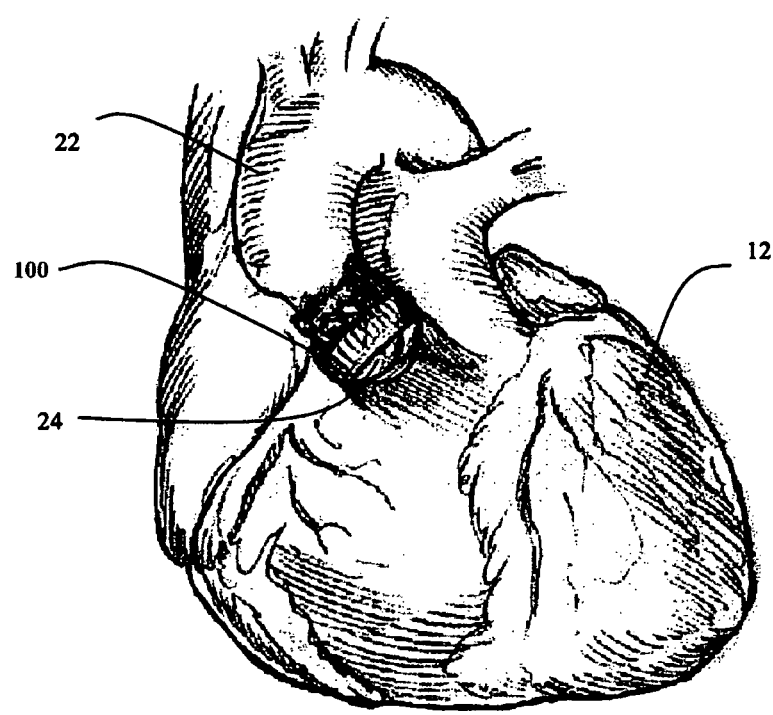
FIG. 8 shows a prosthetic valve implanted in the heart.

FIG. 8 shows an implanted heart valve prosthesis 100 positioned in the aortic valve position.

Figure 9:
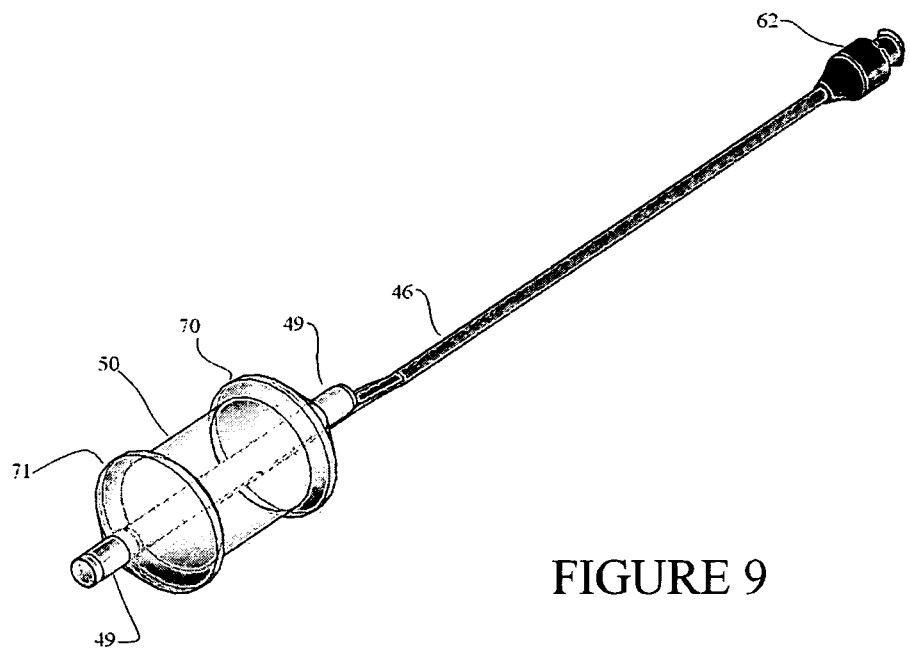
FIG. 9 shows a Scapus™ delivery system.
Figure 10:
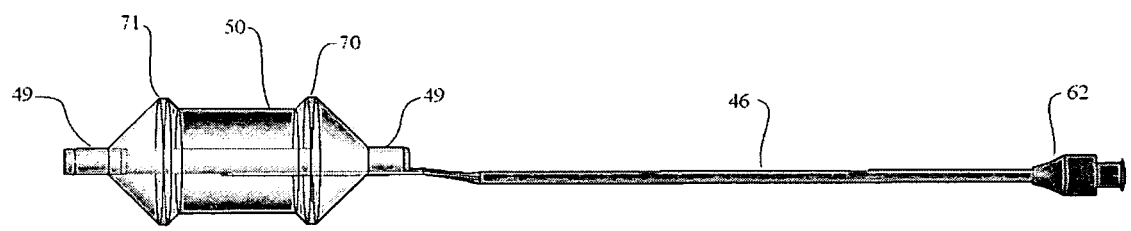
FIG. 10 shows a Scapus™ delivery system.
Figure 11:
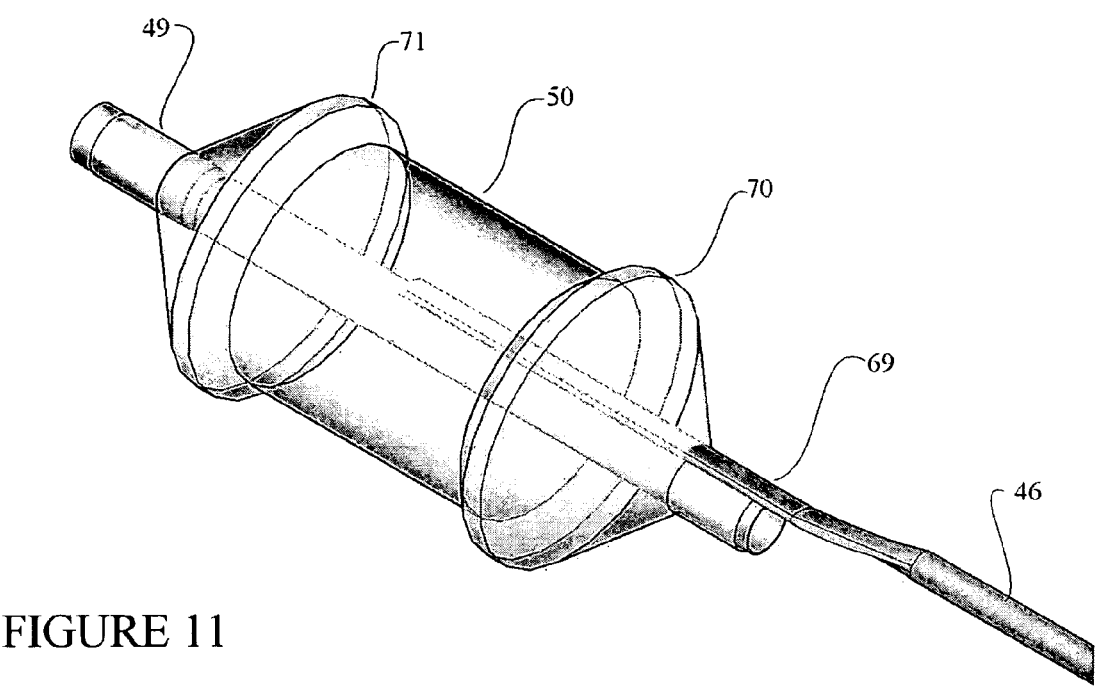
FIG. 11 shows a close-up of a balloon delivery member of a Scapus™ delivery system.

FIGS. 9, 10, and 11 show a Scapus™ delivery system comprising a Scapus™ 46, luer fitting 62, perfusion tube 49 and a dog-bone shaped balloon delivery member 50. The luer fitting 62 is attached to the proximal side of the Scapus™ 46 and may be used to direct fluid for opening and closing the balloon delivery member 50. The balloon delivery member 50 is tightly disposed around the perfusion tube 49. The perfusion tube 49 is attached to the Scapus™ 46. Fluid may flow through the luer fitting 62, through the Scapus™ 46 and into the balloon delivery member 50 to inflate and deflate the balloon.

It is important to note that although the different inventions described herein is typically described in reference to transapical valve implantation, they may also be used in nonbeating heart surgeries. A Scapus™ delivery system, for example, may also be used in a open surgery situation. Thus, in one embodiment of the current invention, a Scapus™ delivery system is used in non-beating heart surgeries. In another embodiment of the current invention, a Scapus™ delivery system may be used in an open chest surgery or robotic surgery.

Converting a Catheter to a Scapus™: Systems and Methods Thereof

The preferred delivery system for delivering heart valves and tools in a trans-apical or trans-heart procedure is a Scapus™ delivery system. If a Scapus™ delivery system is not available, however, one may convert a catheter into a delivery system that is similar to a Scapus™ delivery system.

In one embodiment of the current invention, a substantially thin, stiff guide stick is inserted into the catheter to give it similar characteristics as a Scapus™. The guide-stick is loosely disposed within the catheter and occupies the space that a guidewire would otherwise occupy. But as opposed to a guidewire that cannot resist bending, a guide-stick is substantially rigid and can resist any unintended bending and torsion. A guide-stick disposed within a catheter, in contrast to a catheter by itself, provides sufficient rigidity such that the resulting delivery system may more accurately and more precisely deliver a prosthesis during a beating heart procedure. The resulting delivery system is designed not to bend unless intended by the operator. The resulting delivery system can incorporate junctions or other means of bending at predetermined points to allow the operator to adjust the direction or angle of the delivery path in a controlled fashion.

In another embodiment of the current invention, a substantially stiff guide-sleeve is loosely disposed on the outside of a catheter to give it similar characteristics as a Scapus™ delivery system. The catheter is loosely disposed within the delivery sleeve. The described delivery sleeve is substantially rigid and can resist any unintended bending and torsion. A guide-sleeve loosely disposed on a catheter, in contrast to a catheter by itself, provides sufficient rigidity such that the resulting delivery system may more accurately and more precisely deliver a heart valve prosthesis 100 during a beating heart procedure. The resulting delivery system is designed not to bend unless intended by the operator. The resulting delivery system can incorporate junctions or other means of bending at predetermined points to allow the operator to adjust the direction or angle of the delivery path in a controlled fashion.

Method for Valve Crimping and Valve Preparation

In one embodiment of the present invention, the heart valve prosthesis 100 is shipped to the operating room in an expanded configuration. The heart valve prosthesis 100 is crimped down in diameter using crimpers known to anyone skilled in the art while the heart valve prosthesis 100 is loosely disposed around a delivery member. The crimping process occurs with the operating room or in vicinity of the operating room. The heart valve prosthesis 100 is further delivered to the target site for implantation.

In one embodiment of the current invention, the heart valve prosthesis 100 is shipped to the operating room in a crimped configuration. The heart valve prosthesis 100 is crimped at the manufacturing facility in a careful, consistent, and controlled manner. The heart valve prosthesis 100 may be crimped directly onto a delivery member, such as a balloon delivery member 50. Alternatively, the heart valve prosthesis 100 may be crimped down to a size such that the internal diameter of the heart valve prosthesis 100 matches the external diameter of the delivery member. The heart valve prosthesis 100 remains in a crimped configuration until the heart valve prosthesis 100 reaches the operating room. Crimping the heart valve prosthesis 100 in a controlled environment will minimize structural deterioration to the heart valve prosthesis 100 and will simplify the procedure in the operating room. When reaching the operating room, the crimped heart valve prosthesis 100 is disposed around the delivery member, and the heart valve prosthesis 100 is further delivered to the target site for implantation.

Imaging Systems

Since a transapical procedure does not provide direct line of sight, sufficient imaging of the heart, valves, and other structures is important to provide diagnostics, guidance and feed-back during the procedure. A Scapus™ delivery system may be of a larger diameter than that of a catheter and is thus better suited for containing imaging transducers. Thus in one embodiment of the present invention, an imaging transducer is placed onto the delivery system. In one embodiment of the current invention, the imaging transducer is placed within the delivery member. In another embodiment of the present invention, the imaging transducer is placed just proximal and/or distal to the delivery member.

An external imaging transducer may be provided to view the operating field and imaging systems may be used at any time or throughout the duration of the surgery. The valvuloplasty assembly may include IVUS or other imaging sensors. Such imaging technology can be used to inspect native valve annulus and size the required heart valve prosthesis 100 after valvuloplasty has been completed.

Imaging systems are well-known to anyone skilled in the art and include transesophageal echo, transthoracic echo, intravascular ultrasound imaging (IVUS), intracardiac echo (ICE), or an injectable dye that is radiopaque. Cinefluoroscopy may also be utilized. The placement of imaging probes in relation to a balloon delivery member 50 has previously been described in co-owned PCT/US/04/33026 filed Oct. 6, 2004, incorporated by reference in its entirety.

Valve Removal Systems

The present invention also provides a method or system for removing the native valve with a valve removal device by access through the apical area of the heart. By way of example, the valve removal may be accomplished as taught in co-pending U.S. patent application Ser. Nos. 10/375,718 and 10/680,562, which are incorporated herein by reference as if set forth in their entirety.

In one embodiment of the present invention, the method may further comprise the step of removing at least a portion of the patient's heart valve by means of a cutting tool that is disposed on the Scapus™. In another aspect of the present invention, the cutting tool may be made of an electrically conductive metal that provides radiofrequency energy to the cutting tool for enhanced valve removal. The high frequency energy ablation is well known in the art.

In another embodiment of the present invention, the delivery member includes cutting means comprising a plurality of jaw elements, each jaw element having a sharp end enabling the jaw element to cut through at least a portion of the native valve. In another aspect, the cutting means comprises a plurality of electrode elements, wherein radiofrequency energy is delivered to each electrode element, enabling the electrode element to cut through at least a portion of the native valve. In a further aspect of the present invention, the cutting means comprises a plurality of ultrasound transducer elements, wherein ultrasound energy is delivered to each transducer element enabling the transducer element to cut through at least a portion of the native valve.

A Scapus™ with a valve removal system disposed on it is introduced through the apex and positioned substantially in the vicinity of the aortic valve. The native valve leaflets and debris (e.g. calcium and valve leaflets) are removed. The parts that are not contained by the valve removal systems are caught in the distal embolic protection filter.

Distal Embolic Protection System

The present invention also provides for devices and methods for providing distal embolic protection during the procedure. FIG. 5 and FIG. 6 show examples of distal embolic protection assemblies 68 and its relation to the delivery system 67. It is important that the distal embolic protection filter provides a means for trapping embolic material and debris. In one embodiment, it is also desired that the distal embolic protection filter provides a temporary valve. The filter and temporary valve assembly prevents flush back of blood, embolic material and debris, while still allowing fluid flow into the filter during surgery. The temporary valve may also temporarily do the work of an adjacent heart valve, such as the aortic valve. Thus in one embodiment of the present invention, the distal embolic protection assembly 68 provides a filter member for trapping embolic material that concurrently functions as a temporary valve.

Distal embolic protection assemblies 68 used in both transapical and percutaneous procedures must be compressed and expanded to allow entry into small blood vessels or other body cavities. Combining both a one-way valve and a filter basket mechanism requires a significant amount of hardware making it difficult to compress the filter down sufficiently to be used during trans-apical and percutaneous procedures.

Figure 12:
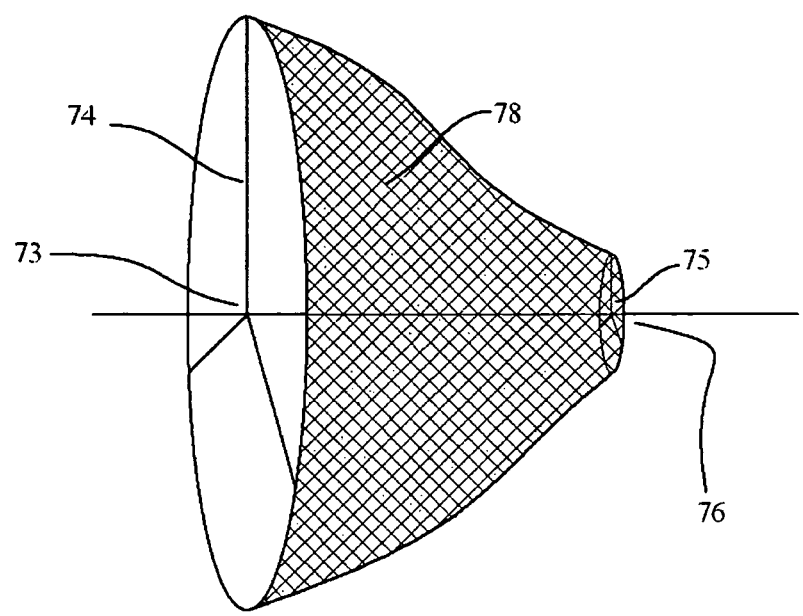
FIG. 12 shows a distal embolic protection subsystem.

FIG. 12 shows a sub-component of a distal embolic protection filter system that incorporates both a filter and the function of a temporary valve. The proximal mouth 73 of the filter consists of a proximal frame 74 that pushes against and makes a seal with the surrounding vasculature. The proximal frame 74 may, for example, push and seal against the inner wall of the aorta, causing all emboli and debris to flow through the filter assembly. In one embodiment of the present invention, the proximal frame 74 is made out of a shape memory alloy such as Nitinol, allowing it to expand into position.

The distal end 76 of the filter sub-assembly is shown open. In other words, debris not caught in the filter mesh 78 may continue out through the distal end 76 of the filter sub-assembly, moving past the distal frame 75. In one embodiment of the present invention, the distal frame 75 is made out of a shape memory alloy such as nitinol, allowing it to maintain an open configuration.

Figure 13:
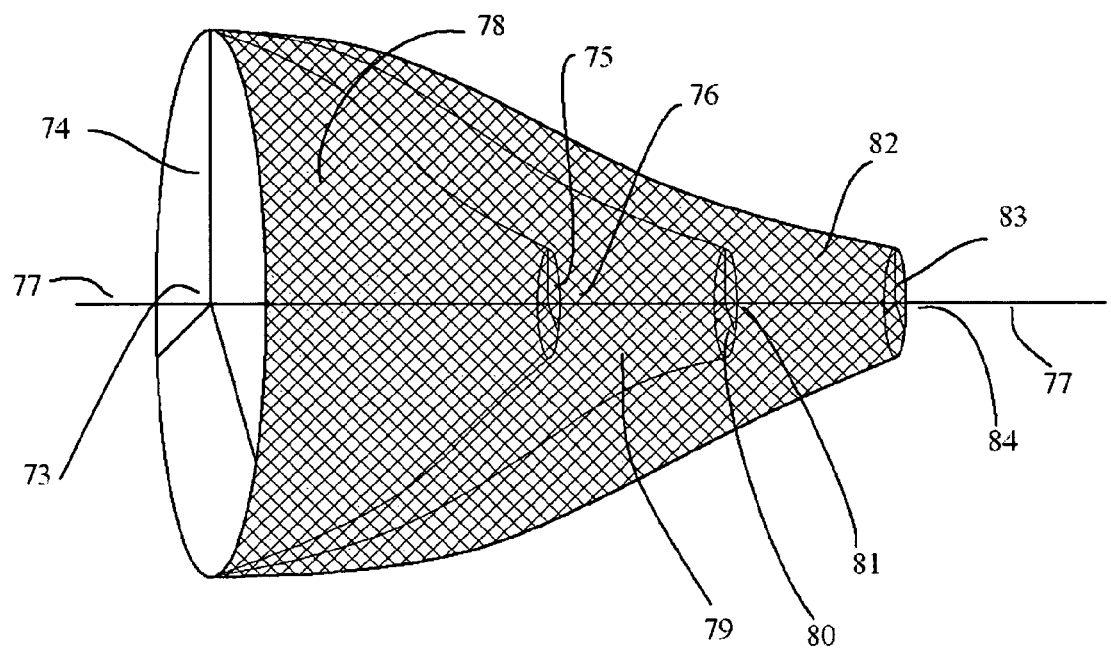
FIG. 13 shows a temporary valve distal embolic protection system.

FIG. 13 shows three inter-connected filter sub-assemblies shown in FIG. 12. Although three sub-assemblies are shown, any number of two or more sub-assemblies will work. The length from the proximal frame to the distal frame of each sub-assembly is slightly different, thus separating the filters meshes of the different filter sub-assemblies 78, 79, and 82. The proximal frame 74 is shared by all the different filter sub-assemblies.

Thus, in one embodiment of the present invention, a plurality of filter sub-assemblies are interconnected at the large inlet of the filters, while the downstream sides of the sub-assemblies have smaller openings allowing debris to flow through. In one embodiment of the current invention, the outermost filter-assembly is closed at the downstream end. As such, the device provides less flow restriction as the blood flows into the porous bags (i.e. downstream from the aortic valve) as opposed to the reverse. This means that the device also functions as a one-way valve.

Valve Decalcification Systems

The formation of atherosclerotic plaques and lesions on cardiovascular tissue, such as blood vessels and heart valves, is a major component of cardiovascular disease. A variety of different methods have been developed to treat cardiovascular diseases associated with calcified atherosclerotic plaques and lesions. Such methods include mechanical removal or reduction of the lesion, such as bypass surgery, balloon angioplasty, mechanical debridement, atherectomy, and valve replacement.

Calcified atherosclerotic plaques and lesions may also be treated by chemical means which may be delivered to the affected area by various catheter devices. For example, U.S. Pat. No. 6,562,020 by Constantz et al., which is incorporated herein by reference as set forth in its entirety, discloses methods and systems for dissolving vascular calcified lesions using an acidic solution. A catheter delivers an acidic fluid to a localized vascular site. Such a system may, for example, decalcify a calcified heart valve by applying an acidic solution (such as hydrochloric acid, etc.)

The current percutaneous anti-calcification system disclosed by Constantz et al. is inserted through the femoral artery. Insertion through the femoral artery is impractical in the case of a trans-apical procedure as it requires another incision into the patient. The system by Constantz et al. may be adapted such that the delivery member controlling and holding the decalcification system is moved from the proximal side (i.e. side of the operator as in the case of femoral access) to the distal side.

Accordingly, in another embodiment of the present invention, the methods and devices of the present invention may be adapted to provide a valve decalcification system, wherein a Scapus™ system is capable of providing the dissolution solution to the treatment site by access through the apical area of the heart. Suitable dissolution solutions are known in the art and are generally characterized as those which are capable of increasing the proton concentration at the treatment site to a desired level sufficient to at least partially dissolve the mineral component of a calcified atherosclerotic lesion.

A trans-apical delivered Scapus™ system may also provide means for isolating the treatment site to prevent the dissolution solution from entering into the patient's circulatory system. Thus in one embodiment of the current invention the decalcification systems described and incorporated for reference above is adapted to be disposed on a Scapus™ as opposed to a catheter. Such means for isolating the treatment site may include a barrier, such as a dual balloon system on the catheter that inflate on both sides of the treatment site.

Figure 14:
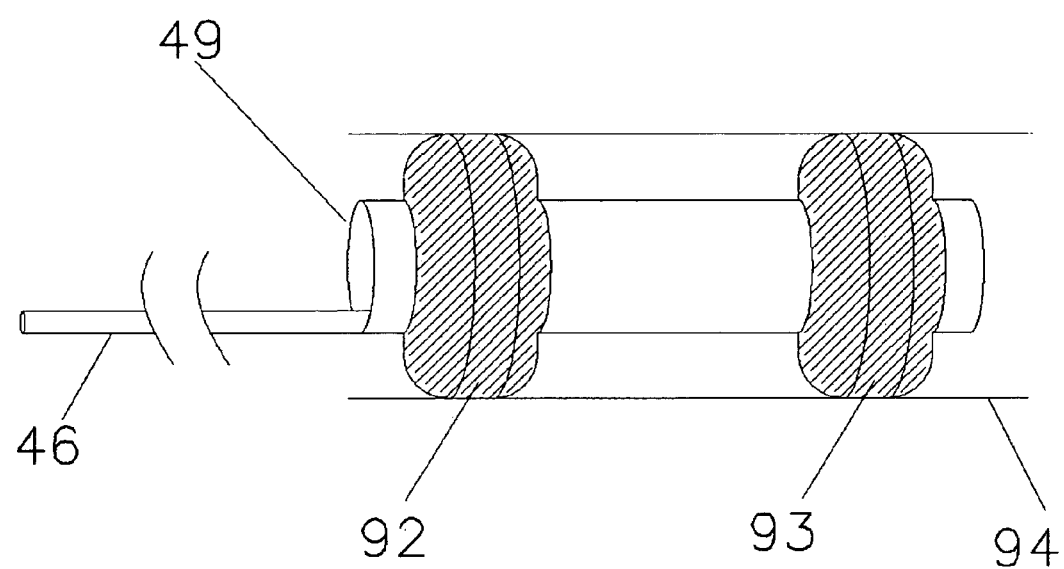
FIG. 14 shows a dual balloon system for providing a valve decalcification system.

FIG. 14 shows such a delivery system where a multilumen Scapus™ 46 connects to a perfusion tube 49 which in turn connects two balloons, a proximal balloon 92 and a distal balloon 93. The two balloons are shown inflated and in intimate contact with the walls of the aorta 94. In one embodiment of the present invention, the perfusion tube 49 is not present and the proximal balloon 92 and the distal balloon 93 are intimately in contact with the Scapus™ 43. Fluid may flow through the Scapus™ 46 to inflate the proximal balloon 92 and distal balloon 93 as well as provide the dissolution solution to the treatment site confined by the proximal balloon 92 and distal balloon 93.

Valve Within Man-Made Valve: Systems And Methods Thereof

It is one objective of the current invention to provide systems and methods for implanting an expandable heart valve within a target valve located within a heart. Such a procedure is beneficial in older or diseased patients who have previously received a valve implant and who cannot or does not want to undergo the trauma of another open heart surgery. Implanting an expandable heart valve within an existing target heart valve allows the use of minimally invasive implantation techniques such as percutaneous or trans-apical valve implantation techniques.

The current methods and systems are distinctly different from Andersen et al. disclosed in U.S. Pat. No. 6,582,462 who describes the implantation of a valve in a body channel or the vasculature. Andersen's intent and objective is to describe an expandable valve that is placed within a body channel or vasculature and uses the intimate contact created within the vasculature, body channel, or native valve as support to allow implantation. In the present invention, an expandable heart valve prosthesis 100 is implanted within a previously implanted man-made heart valve prosthesis and uses the intimate contact created with the previously implanted heart valve prosthesis for support. If the previously implanted heart valve prosthesis is removed, one will concurrently remove the expandable heart valve prosthesis 100 located within the previously implanted heart valve prosthesis.

In one embodiment of the current invention, an expandable heart valve prosthesis 100 is mounted within a previously implanted heart valve prosthesis located within a heart. The expandable heart valve prosthesis 100 may be any valve that can be delivered minimally invasively, such as percutaneous or trans-apically delivered valves. In one embodiment of the current invention, the expandable heart valve prosthesis 100 is a balloon-expandable heart valve. In another embodiment of the present invention, the expandable heart valve prosthesis 100 is the 3F Entrata™ heart valve. In another embodiment of the current invention, the expandable heart valve prosthesis 100 is a self-expandable heart valve. In yet another embodiment of the present invention, the expandable heart valve prosthesis 100 is a valve expanded using some other mechanical or actuating means.

The previously implanted heart valve prosthesis may be any valve either native or man-made. In one embodiment of the current invention, the previously implanted heart valve prosthesis is a mechanical valve. In another embodiment of the present invention, the previously implanted heart valve prosthesis is a tissue valve. The previously implanted heart valve prosthesis may also be made out of polyurethane or be a tissue-engineered valve. In one embodiment of the current invention, the previously implanted heart valve prosthesis can be an expandable heart valve. In yet a further embodiment of the current invention, more than one expandable heart valve prosthesis 100 may be implanted within a previously implanted heart valve prosthesis. As such, multiple minimally invasive heart valve deliveries may be conducted without removing the existing valve or existing valves. The previously implanted heart valve prosthesis may be an aortic valve, mitral valve, pulmonary valve, or a tricuspid valve. The previously implanted heart valve prosthesis may also be a homograft valve or a xenograft valve. Examples of previously implanted heart valve prosthesis include, but are not limited to, the Edwards Perimount Valve, the Edwards BioPhysio Valve, the Medtronic Hancock I Valve, the Medtronic Hancock M.O. Valve, the Medtronic Hancock II Valve, the Medtronic Mosaic Valve, the Medtronic Intact Valve, the Medtronic Freestyle Valve, the St. Jude Toronto Stentless Porcine Valve (SPV), and the St. Jude Prima Valve.

The expandable heart valve prosthesis 100 may be made to fit well within the previously implanted heart valve prosthesis. In one instance, the posts of the expandable heart valve prosthesis 100 are coordinated to fit the posts of the previously implanted heart valve prosthesis. Thus in one embodiment of the present invention, the posts of the expandable heart valve prosthesis 100 matches the orientation for the posts of the previously implanted heart valve prosthesis. In one embodiment of the present invention, the inter-post separation angles of the expandable heart valve prosthesis 100 add up to 360°. In other embodiments of the present invention, the inter-post separation angle of the heart valve prosthesis 100 is 120°, 120°, and 120°; or 135°, 120°, and 105°; or 135°, 105°, and 120°; or 120°, 135°, and 105°; or 120°, 105°, and 135°; or 105°, 135°, and 120°; or 105°, 120°, and 135°.

Figure 15:
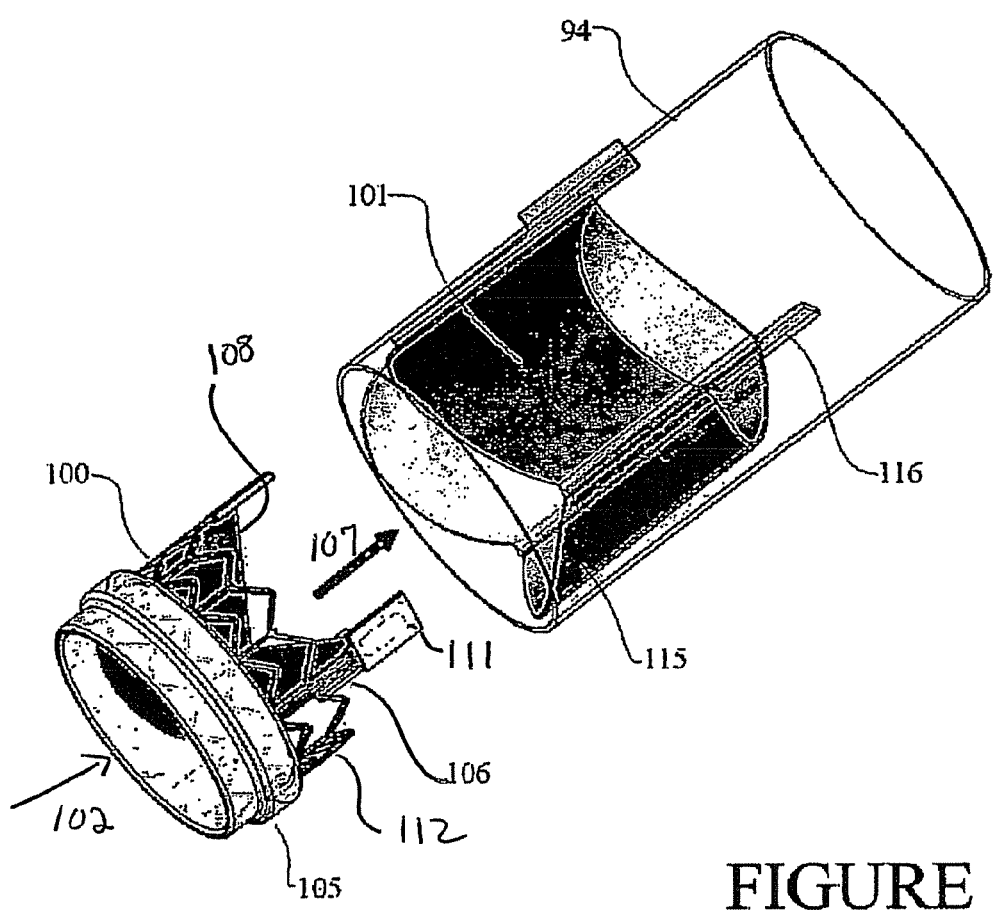
FIG. 15 shows an exploded view of a heart valve implanted inside a previously implanted heart valve.
Figure 16:
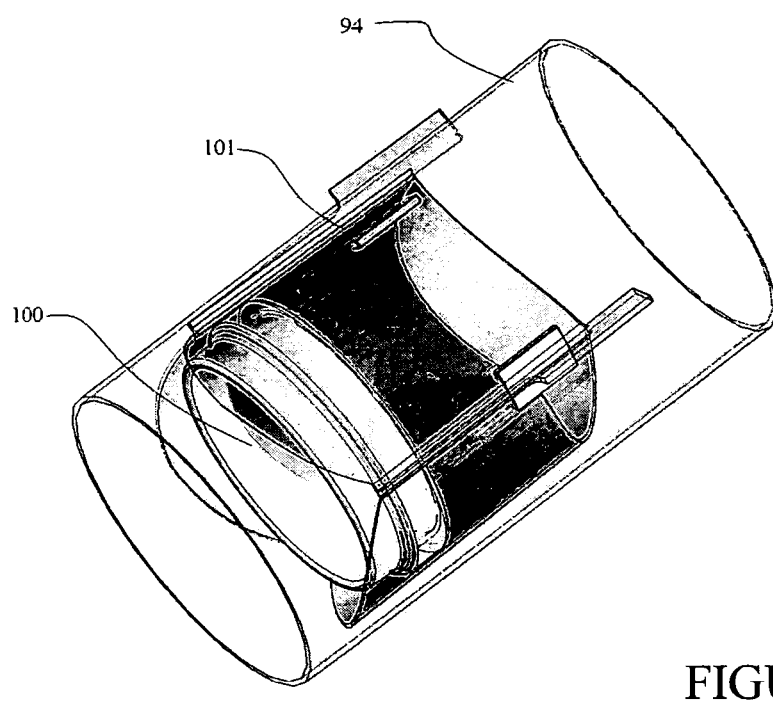
FIG. 16 shows an a heart valve implanted inside a previously implanted heart valve.

FIG. 15 shows an exploded view of FIG. 16 where a heart valve prosthesis 100 is shown implanted within a previously implanted heart valve prosthesis 101. In a preferred embodiment, the inflow ring or annulus 105 of the heart valve prosthesis 100 is aligned with the inflow ring or annulus 115 of the previously implanted heart valve prosthesis 101. In another preferred embodiment, the commissural posts 106 of the heart valve prosthesis 100 is aligned with the commissural posts 116 of the previously implanted heart valve prosthesis 101. As depicted in FIGS. 4 and 15 the heart valve prosthesis includes a pliant prosthetic valve 100 having an inlet end 102, an outlet end 107, a plurality of leaflet portions 108 and a plurality of commissural tabs 111 positioned at the outlet end 107 and integrally formed with said leaflet portions 108. A collapsible stent 112 is positioned about the exterior of the valve 100, the collapsible stent having a circular inflow rim and a circular outflow rim connected by a plurality of commissural posts 106 (also referred to as longitudinal support posts). The plurality of commissural tabs 111 are operably coupled to the commissural posts 106.

It should be noted that although reference is made herein to a heart valve 100 implanted into a previously implanted heart valve prosthesis 101 inside the aorta, it is intended for such valve procedures to encompass any location within the heart 12, and not to be limited to the aorta.

In a preferred embodiment of the current invention, the previously implanted heart valve prosthesis 101 is the same size or one size larger than the expandable heart valve prosthesis 100. For purpose of example, if the previously implanted heart valve prosthesis 101 is 27 mm, the expandable heart valve prosthesis 100 is either 25 mm or 27 mm in size. Thus, in one embodiment of the current invention, the expandable heart valve prosthesis 100 is the same size as the previously implanted heart valve prosthesis 101. In another embodiment of the current invention, the expandable heart valve prosthesis 100 is larger than the previously implanted heart valve prosthesis 101. In another embodiment of the current invention, the expandable heart valve prosthesis 100 is smaller than the previously implanted heart valve prosthesis 101.

Clinical records will specify the exact size used during an earlier implant. The size of the previously implanted heart valve prosthesis 101 will thus be known. In-vitro tests will show the best size expandable heart valve prosthesis 100 for a specific size and type target valve. The optimal size expandable heart valve can thus be determined from the clinical records from the previous heart valve implant. Thus in one embodiment of the present invention, the size of the expandable heart valve prosthesis 100 to be used is determined from clinical records of prior implants.

In one embodiment of the current invention, an expandable stent is implanted within a previously implanted heart valve prosthesis 101 prior to implanting the expandable heart valve prosthesis 100. In another embodiment of the current invention, valvuloplasty is used to expand the orifice of the previously implanted heart valve prosthesis 101 before implanting an expandable heart valve prosthesis 100 or before implanting an expandable stent.

Any delivery system may be used to deliver the expandable heart valve prosthesis 100. In one embodiment of the current invention, the delivery system is a catheter. In another embodiment of the current invention, the delivery system is a Scapus™. The expandable heart valve prosthesis 100 may be delivered through any access point to the heart. In one embodiment of the present invention, the expandable heart valve prosthesis 100 is delivered minimally invasively. In one embodiment of the present invention, the expandable heart valve prosthesis 100 is delivered percutaneously. In another embodiment of the present invention, the expandable heart valve prosthesis 100 is delivered trans-apically.

Sutureless Valve Inserter System And Methods Thereof

The benefits of a Scapus™ valve delivery system may also be utilized in the case of self-expandable valves. As such, the delivery system may be used for percutaneous valve delivery, trans-apical valve delivery, trans-heart delivery. In addition to these delivery techniques, the Scapus™ delivery system may be utilized in more invasive cardiac procedures such as open heart procedures.

The Scapus™ delivery system is well suited for delivering the 3F Enable Aortic Heart Valve™ and the other valves described in co-owned U.S. applications entitled "Minimally Invasive Valve Replacement System" with the following application Ser. Nos. 10/680,733; 10/680,719; 10/680,728; 10/680,560; 10/680,716; 10/680,717; 10/680,732; 10/680,562; 10/680,068; 10/680,075; 10/680,069; 10/680,070; 10/680,071; and 10/680,567, all incorporated herein for reference in their entirety.

Sutureless Valve Inserter System And Methods Thereof

Current tissue heart valve replacements gradually calcify after implanted in the heart. Such is also the case when implanting replacement heart valves in animals such as pigs or sheep. In fact, replacement heart valves intended for human use typically calcify faster when implanted in animals such as pigs or sheep. Because of difference in flow dynamics, physiology, and biochemistry, the best performing commercially available heart valves will typically show signs of calcification in pigs and sheep within 10-200 days. Standard animal models used for pre-clinical valve testing is frequently sheep, but pigs may also be used. Adolescent sheep have great propensity to calcify bioprosthetic valves.

The fact that cardiac valves places in the heart of certain animal models calcify quickly may be used as basis for creating calcified animal models for use in the development and testing of cardiac valves.

Open heart surgery valve replacement on adolescent sheep typically results in less than 40% success/survival in the aortic position, owing to the very small valve sizes and the use of full bypass. Open heart surgery valve replacement on adolescent sheep typically results in more than 80% success/survival in the mitral position owing to the larger valve sizes and the use of beating heart, partial bypass. Placing replacement valves in the mitral position during animal testing is not just used to reduce costs but is also considered a "worst-case" position due to higher backpressures. Replacement aortic and mitral valves are therefore frequently placed in the mitral position during animal studies.

Accordingly, it is one object of the present invention to provide methods and systems for the creation of a calcified animal model. Commercially available tissue valves are first implanted in adolescent sheep. The animals are survived for 10-200 days and the performance evaluated. Because of the increased propensity for calcification in animals, all the valves implanted are expected to be stenotic and/or incompetent due to calcification of tissue leaflets. Sheep may be evaluated at regular intervals using echo.

It is another object of the present invention to utilize the calcification model described above in the development and testing of cardiac valves. Using either a percutaneous or trans-apical implant techniques, place replacement heart valves within the calcified valves of adolescent sheep. Survive the test animals for 20 weeks (150+/−10 days) or as required by regulatory authorities. Monitor the replacement valves. Necropsy, pathology, and post mortem histology may be performed.

The present invention may be divided in two phases:
I. Create a calcified animal model by replacing the native valves of adolescent sheep with commercially available valves and surviving the animals for 10-200 days.
II. Implant minimally invasive valves within the calcified valve orifices using a minimally invasive valve procedure.

In phase I of the invention, a calcified animal model is created by replacing the native valves of adolescent sheep with commercially available valves and surviving the animals. In one embodiment of the present invention, the heart valve replacement procedure is an on-pump procedure. In another embodiment of the present invention, the heart valve replacement procedure is a minimally invasive heart valve procedure, such as a percutaneous heart valve replacement procedure, or a trans-apical valve procedure. In the latter embodiment, the method described herein would allow testing of a minimally invasive heart valve repeat-procedure. In one embodiment of the current invention, the heart valve replacement procedure is conducted endoscopically. In yet another embodiment of the current invention, the heart valve replacement procedure is conducted using robots.

In one embodiment of the present invention, drugs are utilized to adjust the rate of calcification. In another embodiment, the valve implanted during Phase I is coated with a chemical substance used to adjust the rate of calcification.

Any valve may be implanted during Phase I. In one embodiment of the present invention, the valve implanted is a tissue valve. In another embodiment of the present invention, the valve implanted is a mechanical valve. Implanted heart valves may include aortic valves, mitral valves, tricuspid valves, or pulmonary valves. A replacement valve may not necessarily be implanted in its intended position. As an example, an aortic valve may be implanted in the mitral position of the animal. Thus in one embodiment of the present invention, a replacement aortic valve is implanted in the mitral position. In one embodiment of the current invention, multiple valves are implanted in different positions at the same time.

In a preferred embodiment of the current invention, valves are implanted in animals whose heart physiology and flow dynamics, as well as biochemistry, match humans as close as possible. Sheep and pigs are thus frequently used for heart valve testing. Thus, in one embodiment of the current invention, sheep is used as the animal model. In another embodiment of the current invention, pigs are used as the animal model. Any other primate may be used as an animal model. In one embodiment of the current invention, animals of subclass eutheria are used as the animal model. In another embodiment of the current invention, animals of the suborder anthropoidea (e.g. monkeys and apes).

The age of an animal affects the rate of calcification. Thus, in one embodiment of the current invention, the age of the animal is the equivalent of adolescence. In another embodiment of the current invention, the animals used are adults.

It is one object of the current invention to survive sufficient animals to the end of Phase II such that pre-clinical regulatory requirements are met for different regulatory bodies. It is expected that some animals will not survive the valve replacements during phase I. Further animals may perish during the duration of Phase I. Further animals will perish during the replacement implants during Phase II as well as during the duration of Phase II. In one preferred embodiment of the present invention, an excess number of animals are used to start Phase I such that sufficient numbers of animals are survived all the way through Phase II. The exact number of animals needed for the start of Phase I depends on numerous variables including the operator, the type of animal, the type of procedures.

It is one object of the current invention to monitor the progression of calcification and diseases related to implanted valves. Different monitoring equipment such as ultrasound, MRI, CT, and cinefluoroscopy, are used during the course of Phase I and Phase II. In one embodiment of the present invention, echo is used at 60, 90, and 120 days during Phase I to monitor the implanted valves.

In one embodiment of the present invention, the animals in Phase I are survived for 90-120 days. The length of Phase I depends on factors such as what type of animal used and what type of tissue valves used. The valves may be monitored during Phase I. It may be possible to go to Phase II earlier based upon in-vivo evaluation.

In Phase II of the invention, valves are implanted within the calcified valve orifices. Implant procedures include, but are not limited to minimally invasive valve procedures, percutaneous valve procedures, trans-apical valve procedure, on-pump valve procedure, endoscopic valve procedure, and robotic valve procedure.

In one embodiment of the present invention, drugs are utilized to adjust the rate of calcification. In another embodiment, the valve implanted during Phase II is coated with a chemical substance used to adjust the rate of calcification.

Any valve may be implanted during Phase II. Tissue valves include, but are not limited to tissue valve, mechanical valves, aortic valves, mitral valves, tricuspid valves, pulmonary valves. A replacement valve may not necessarily be implanted in its intended position. As an example, an aortic valve may be implanted in the mitral position of the animal. Thus in one embodiment of the present invention, a replacement aortic valve is implanted in the mitral position.

In one embodiment of the present invention, the animals in Phase I are survived for 20 weeks (150+/−10 days). The length of Phase II depends on guidelines provided by regulatory bodies.

In one embodiment of the current invention, the minimally invasive valve delivery is conducted using a SCAPUS™ delivery system. In one embodiment of the present invention, the valve utilized is the 3F Therapeutics, Inc. Entrata™ valve. In one embodiment of the present invention, a balloon is used in the inferior vena cava to regulate pressure during the procedure.

In one embodiment of the current invention, the replacement valve in Phase II is seated within the calcified valve orifice of the valve replacement conducted in Phase I. In another embodiment of the present invention, the replacement valve in Phase II is seated just upstream from the calcified valve orifice of the valve replacement conducted in Phase I. In another embodiment of the present invention, the replacement valve in Phase II is seated just downstream from the calcified valve orifice of the valve replacement conducted in Phase I.

Obviously, numerous variations and modifications can be made within departing from the spirit of the present invention. Therefore, it should be clearly understood that the forms of the present invention described above and shown in the figures of the accompanying drawings are illustrative only and are not intended to limit the scope of the present invention.

We claim:

1. A delivery system comprising:
an elongated, rigid, rod-shaped support structure;
a balloon delivery member coupled to the support structure at a distal portion of the support structure;
a valve replacement detachably positioned about the balloon delivery member and structured to be collapsed to temporarily reduce a valve diameter, said valve replacement comprising a pliant prosthetic valve having an inlet end, an outlet end, a plurality of leaflet portions and a plurality of commissural tabs positioned at the outlet end and integrally formed with said leaflet portions; and
a collapsible stent positioned about an exterior of the valve, the collapsible stent having a circular inflow rim and a circular outflow rim connected by a plurality of longitudinal support posts, said commissural tabs operably coupled to said longitudinal support posts,
wherein said rigid support structure is configured to transmit longitudinal and rotational motion along its length without twisting or bending along its length,
wherein the balloon delivery member comprises a perfusion tube connecting a distal end and a proximal end of the balloon delivery member and structured to allow blood flow through the balloon delivery member, and
wherein the rigid support structure terminates between a proximal end of a balloon of the balloon delivery member and a distal end of the balloon of the balloon delivery member.

2. The delivery system of claim 1 wherein the stent is made of stainless steel.

3. The delivery system of claim 1 wherein the stent has three parallel support posts attached to the circular inflow and outflow rims at about 120° intervals, 4. The delivery system of claim 1 wherein the rigid support structure is selected from the group consisting of a solid rod, a hollow rod, a catheter with a guide stick, and a catheter with a guide sleeve.

5. The delivery system of claim 4 wherein the hollow rod includes one or more lumens therewithin.

6. The delivery system of claim 1, wherein the rigid support structure is fabricated from the group consisting of stainless steel and a polymer.

7. The delivery system of claim 1 wherein the longitudinal support posts are adapted to align with the commissural attachments of a diseased heart valve.

8. The delivery system of claim 1 wherein said balloon delivery member includes a first inflatable balloon delivery portion positioned at a distal end of the valve, which in an inflated configuration has a diameter larger than a diameter of the valve; and a second inflatable balloon delivery portion positioned about the rigid support structure at a proximal end of the valve, which in the inflated configuration has a diameter larger than the diameter of the valve.

9. The delivery system of claim 8 wherein the perfusion tube is positioned about the rigid support structure and within the first inflatable balloon delivery portion, the perfusion tube being operably connected to one or more holes in the first inflatable balloon delivery portion, wherein said perfusion tube is structured to allow blood flow through the perfusion tube.

10. The delivery system of claim 8 wherein said first and second balloon delivery portions comprise separate balloon delivery portions.

11. The delivery system of claim 8 wherein the balloon delivery member further includes a middle portion that is disposed within the valve and connects said first and second balloon delivery portions.

12. The delivery system of claim 11 wherein the first and second inflatable balloon delivery portions have a larger coefficient of friction than the balloon delivery member middle portion.

13. The delivery system of claim 11 wherein the perfusion tube is positioned about the rigid support structure and is operably connected to the first balloon delivery portion, the second balloon delivery portion and the middle connecting portion, wherein the perfusion tube is structured to allow blood flow through the perfusion tube.

14. The delivery system of claim 11 wherein a balloon inflation device, adapted to inflate the first and second inflatable balloon delivery portions and the balloon delivery middle portion, is secured to an exterior of the rigid support structure at a plurality of locations.

15. The delivery system of claim 14 wherein said first balloon delivery portion, said second delivery portion and said middle portion are integrally formed.

16. The delivery system of claim 1 wherein the valve replacement is structured to be folded to temporarily reduce the valve diameter by up to about 90%.

17. The delivery system of claim 1 wherein the stent is fabricated from a shape memory alloy having an Af temperature between about 0° C. and about 30° C.

18. The delivery system of claim 17 wherein the shape memory alloy is Nitinol.

19. The delivery system of claim 1, wherein the rigid support structure is further structured and arranged to deliver the valve replacement during a beating heart procedure.

20. The delivery system of claim 1, wherein the rigid support structure is coupled to an exterior surface of the perfusion tube.

21. The delivery system of claim 1, wherein the support structure cannot be bent by forces imposed by blood flow and a beating heart.

22. The delivery system of claim 1, wherein the support structure provides rigid support between a proximal portion of the support structure and the distal portion of the support structure located in the heart during a beating heart procedure.

23. A delivery system comprising:
- an elongated, rigid, rod-shaped support structure having a proximal end and a distal end;
- a balloon delivery member positioned about the support structure at a distal portion of the support structure;
- a valve replacement detachably positioned about the balloon delivery member and structured to be collapsed to temporarily reduce a valve diameter; and
- a collapsible stent positioned about an exterior of the valve, the collapsible stent having a circular inflow rim and a circular outflow rim connected by a plurality of longitudinal support posts,
- wherein the proximal and distal ends of the support structure maintain longitudinal and rotational position and orientation with respect to each other,
- wherein the balloon delivery member comprises a perfusion tube connecting a distal end and a proximal end of the balloon delivery member and structured to allow blood flow through the balloon delivery member, and
- wherein the support structure terminates between a proximal end of a balloon of the balloon delivery member and a distal end of the balloon of the balloon delivery member.

24. The delivery system of claim 23, wherein the support structure provides rigid support between the proximal end of the support structure and the distal end of the support structure located in the heart during a beating heart procedure.

25. A scapus delivery system comprising:
- an elongated, rigid scapus;
- a balloon delivery member positioned about the scapus;
- a heart valve replacement detachably positioned about the balloon delivery member and structured to be collapsed to temporarily reduce a valve diameter; and
- a collapsible stent positioned about an exterior of the valve, the collapsible stent having a circular inflow nm and a circular outflow rim connected by a plurality of longitudinal support posts,
- wherein said rigid scapus is structured to precisely longitudinally and rotationally position said valve replacement in an aorta transapically,
- wherein the scapus is configured to resist bending and torsion,
- wherein the balloon delivery member comprises a perfusion tube connecting a distal end and a proximal end of the balloon delivery member and structured to allow blood flow through the balloon delivery member, and
- wherein the scapus terminates between a proximal end of a balloon of the balloon delivery member and a distal end of the balloon of the balloon delivery member.

26. The delivery system of dam 25, wherein the scapus provides rigid support between a proximal portion of the scapus and a distal portion of the scapus located in the heart during a beating heart procedure.

* * * * *

UNITED STATES PATENT AND TRADEMARK OFFICE
CERTIFICATE OF CORRECTION

PATENT NO. : 8,790,396 B2  
APPLICATION NO. : 11/492486  
DATED : July 29, 2014  
INVENTOR(S) : Bergheim et al.

It is certified that error appears in the above-identified patent and that said Letters Patent is hereby corrected as shown below:

In the Claims,

In Claim 25, column 26, lines 15,16  
"circular inflow nm and a circular outflow" should read -- "circular inflow rim and a circular outflow" --

In Claim 26, column 26, line 30  
"The delivery system of dam 25, wherein the" should read -- The delivery system of claim 25, wherein the --

Signed and Sealed this  
Twenty-first Day of July, 2015

Michelle K. Lee  
*Director of the United States Patent and Trademark Office*